(12) United States Patent
Kim et al.

(10) Patent No.: US 8,242,242 B2
(45) Date of Patent: Aug. 14, 2012

(54) PREPARATION OF AN ARTIFICIAL TRANSCRIPTION FACTOR COMPRISING ZINC FINGER PROTEIN AND TRANSCRIPTION FACTOR OF PROKARYOTE, AND A USE THEREOF

(75) Inventors: Sun-Chang Kim, Daejeon (KR); Ju-Young Lee, Daejeon (KR); Bong-Hyun Sung, Daejeon (KR); Jun-Hyoung Lee, Daejeon (KR); Sang-Hee Lee, Daejeon (KR); Kui-Hyeon Kang, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 530 days.

(21) Appl. No.: 12/444,842

(22) PCT Filed: Dec. 15, 2006

(86) PCT No.: PCT/KR2006/005493
§ 371 (c)(1),
(2), (4) Date: Apr. 8, 2009

(87) PCT Pub. No.: WO2008/050935
PCT Pub. Date: May 2, 2008

(65) Prior Publication Data
US 2010/0136663 A1    Jun. 3, 2010

(30) Foreign Application Priority Data

Oct. 24, 2006 (KR) .................. 10-2006-0103675

(51) Int. Cl.
*C12N 1/21* (2006.01)
(52) U.S. Cl. ............... 530/350; 506/18; 435/252.33; 530/402
(58) Field of Classification Search ............... None
See application file for complete search history.

(56) References Cited

U.S. PATENT DOCUMENTS

| | | | | |
|---|---|---|---|---|
| 5,096,815 A | * | 3/1992 | Ladner et al. | 435/69.1 |
| 5,198,346 A | * | 3/1993 | Ladner et al. | 435/69.1 |
| 5,670,317 A | * | 9/1997 | Ladanyi et al. | 435/6.16 |
| 5,891,687 A | * | 4/1999 | Schlieper et al. | 435/471 |

(Continued)

FOREIGN PATENT DOCUMENTS

JP    2002-505111    2/2002

(Continued)

OTHER PUBLICATIONS

Lee, D et al, Current Topics in Medical Chemistry, 2003, vol. 3, pp. 339-353.*

(Continued)

*Primary Examiner* — Albert Navarro
*Assistant Examiner* — Ginny Portner
(74) *Attorney, Agent, or Firm* — Morrison & Foerster LLP

(57) ABSTRACT

The present invention relates to an artificial transcription factor which can artificially regulate gene expression of an *E. coli*, wherein the transcription factor comprising zinc finger proteins and transcription factors of prokaryote, and to be engineered *E. coli* using the same. Specifically, the artificial transcription factors comprising zinc finger domains and transcription factors in *E. coli* as effector domains are prepared and said artificial transcription library is introduced to *E. coli* to effectively and artificially regulate gene expression regardless of an activity of endogenous transcription factors in the *E. coli* and to induce *E. coli* having various desired phenotypes. Thus, only *E. coli* having the desired phenotypes useful for industries can be selected and used.

5 Claims, 10 Drawing Sheets

U.S. PATENT DOCUMENTS

| | | | |
|---|---|---|---|
| 5,905,146 A * | 5/1999 | Lecka-Czernik | 536/23.5 |
| 6,140,466 A * | 10/2000 | Barbas et al. | 530/350 |
| 6,479,626 B1 * | 11/2002 | Kim et al. | 530/300 |
| 6,733,970 B2 * | 5/2004 | Choo et al. | 435/6.12 |
| 6,790,941 B2 | 9/2004 | Barbas, III | |
| 6,943,241 B2 * | 9/2005 | Isogai et al. | 536/23.1 |
| 7,379,932 B2 * | 5/2008 | Agrawal et al. | 707/710 |
| 7,514,257 B2 * | 4/2009 | Lee et al. | 435/325 |
| 7,745,391 B2 * | 6/2010 | Mintz et al. | 514/19.3 |
| 2002/0061512 A1 * | 5/2002 | Kim et al. | 435/4 |
| 2003/0049799 A1 * | 3/2003 | Schwartz et al. | 435/69.7 |
| 2003/0165997 A1 * | 9/2003 | Kim et al. | 435/7.1 |
| 2003/0194704 A1 * | 10/2003 | Penn et al. | 435/6 |
| 2003/0194727 A1 * | 10/2003 | Kim et al. | 435/6 |
| 2004/0010119 A1 * | 1/2004 | Guo et al. | 530/350 |
| 2004/0029144 A1 * | 2/2004 | Nguyen et al. | 435/6 |
| 2004/0209277 A1 * | 10/2004 | Lee et al. | 435/6 |
| 2004/0259258 A1 * | 12/2004 | Kim et al. | 435/488 |
| 2005/0282193 A1 * | 12/2005 | Bulyk et al. | 435/6 |
| 2007/0042378 A1 * | 2/2007 | Kim et al. | 435/6 |
| 2007/0087371 A1 * | 4/2007 | Kim et al. | 435/6 |

FOREIGN PATENT DOCUMENTS

| | | | |
|---|---|---|---|
| JP | 2003-523195 | | 8/2003 |
| JP | 2005-500068 | | 1/2005 |
| JP | 2005-511049 | | 4/2005 |
| WO | WO-01/60970 | | 8/2001 |
| WO | 02-24895 | * | 3/2002 |
| WO | WO-03/104414 | | 12/2003 |
| WO | WO-2004/108883 | | 12/2004 |
| WO | 2005-061705 | * | 7/2005 |
| WO | 2005-111060 | * | 11/2005 |
| WO | WO-2007/081647 | | 7/2007 |

OTHER PUBLICATIONS

Zhou, Y et al, PNAS, 1993, vol. 90, pp. 6081-6085.*
Bae et al., Nat. Biotechnol. (2003) 21(3):275-280.
Beerli et al., PNAS USA (1998) 95:14628-14633.
Beerli et al., PNAS USA (2000) 97(4):1495-1500.
International Search Report for PCT/KR2006/005493, mailed on Jul. 23, 2007, 4 pages.
Joung et al., PNAS USA (2000) 97(13):7382-7387.
Liu et al., PNAS USA (1997) 94:5525-5530.
Lund et al., J. Mol. Biol. (2004) 340(3):599-613.
Park et al., J. Bacteriol. (2005) 187(15):5496-5499.
Written Opinion of the International Searching Authority for PCT/KR2006/005493, mailed on Jul. 23, 2007, 4 pages.
Harman, "Allosteric regulation of the cAMP receptor protein," Biochimica et Biophysica Acta (2001) 1547:1-17.
Notice of Reasons for Rejection (translation) for JP 2009-533228, mailed Jul. 19, 2011, 5 pages.
Park et al., "Phenotypic alteration of eukaryotic cells using randomized libraries of artificial transcription factors," Nature Biotechnology (2003) 21(10):1208-1214.

* cited by examiner

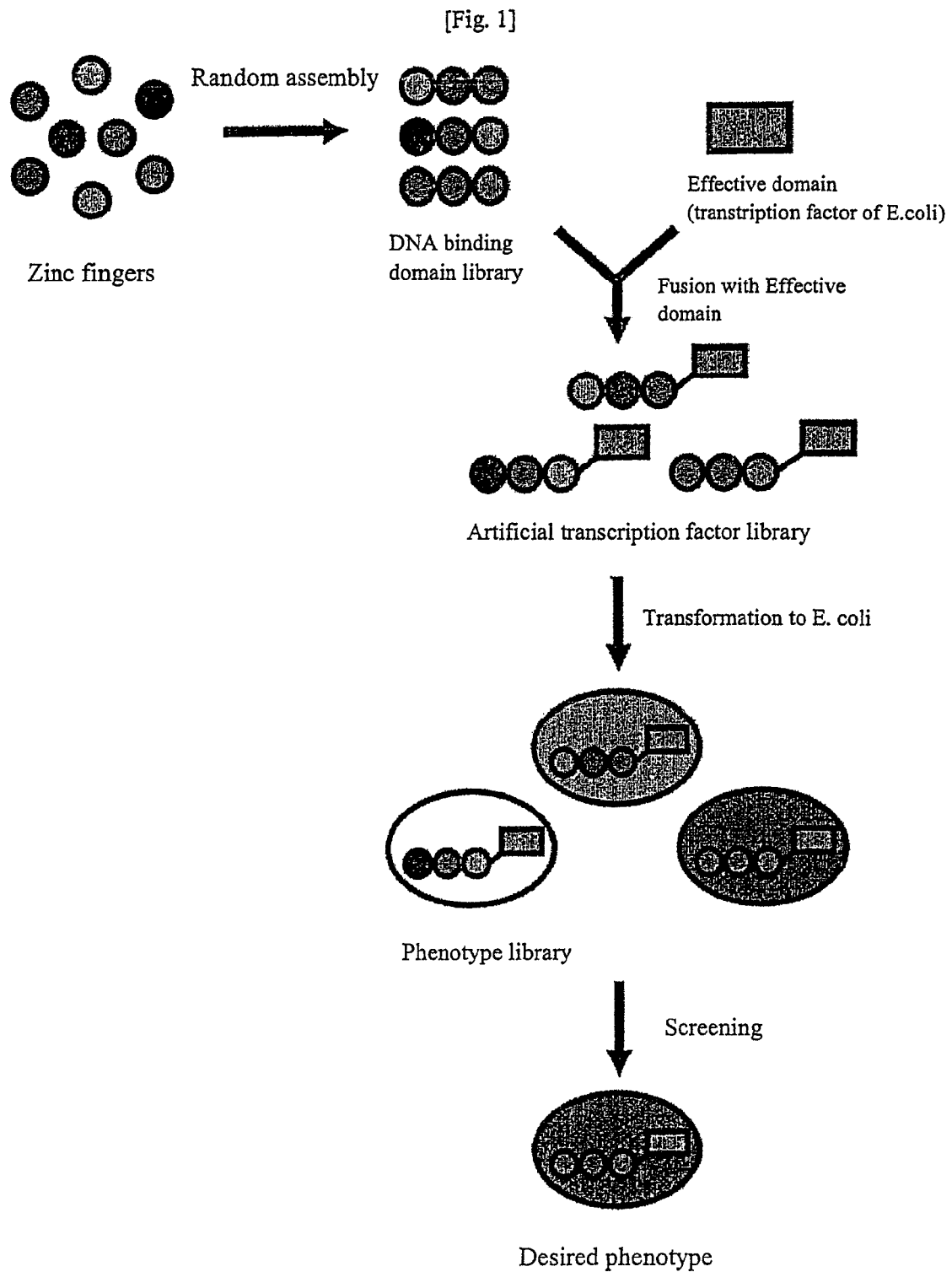

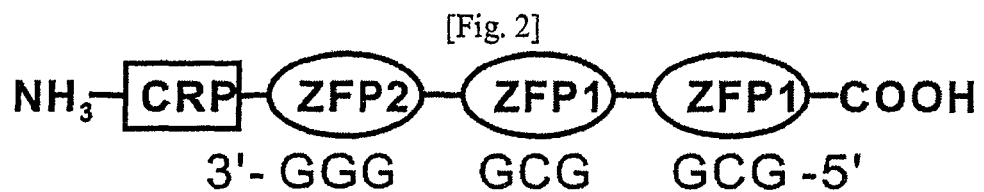
[Fig. 2]
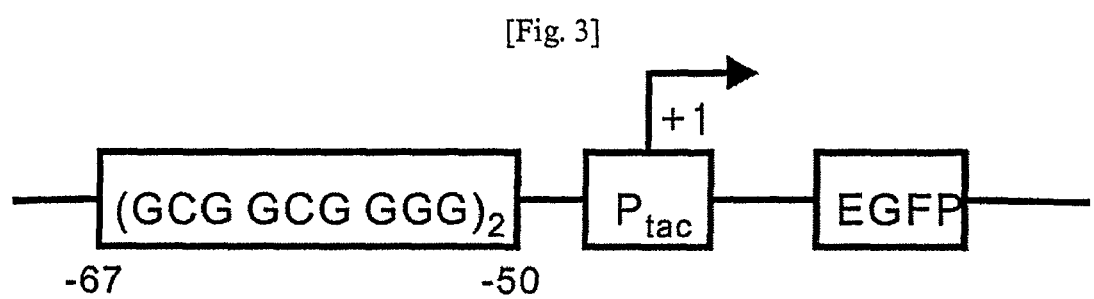
[Fig. 3]
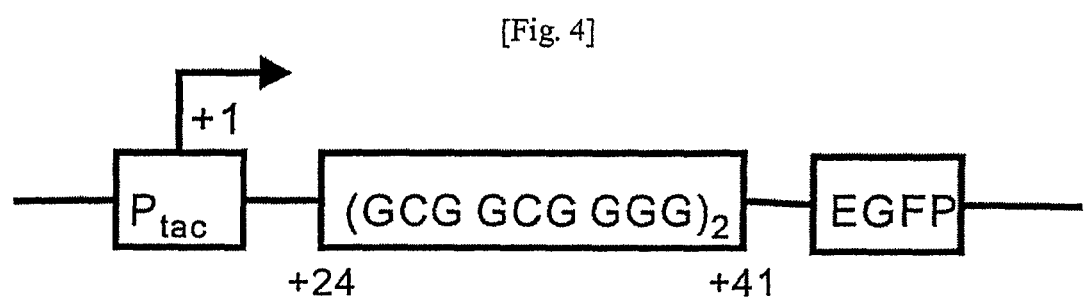
[Fig. 4]

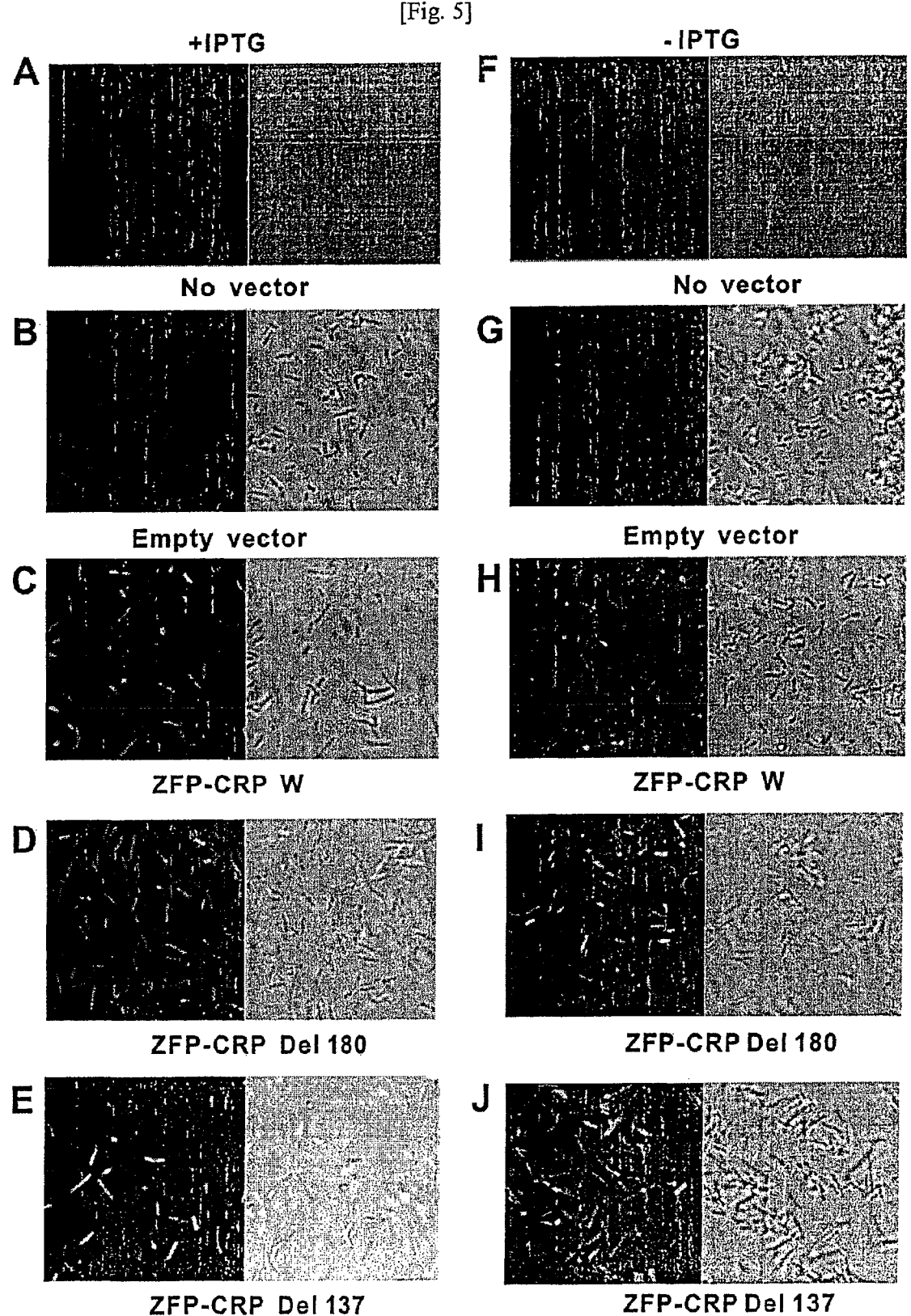

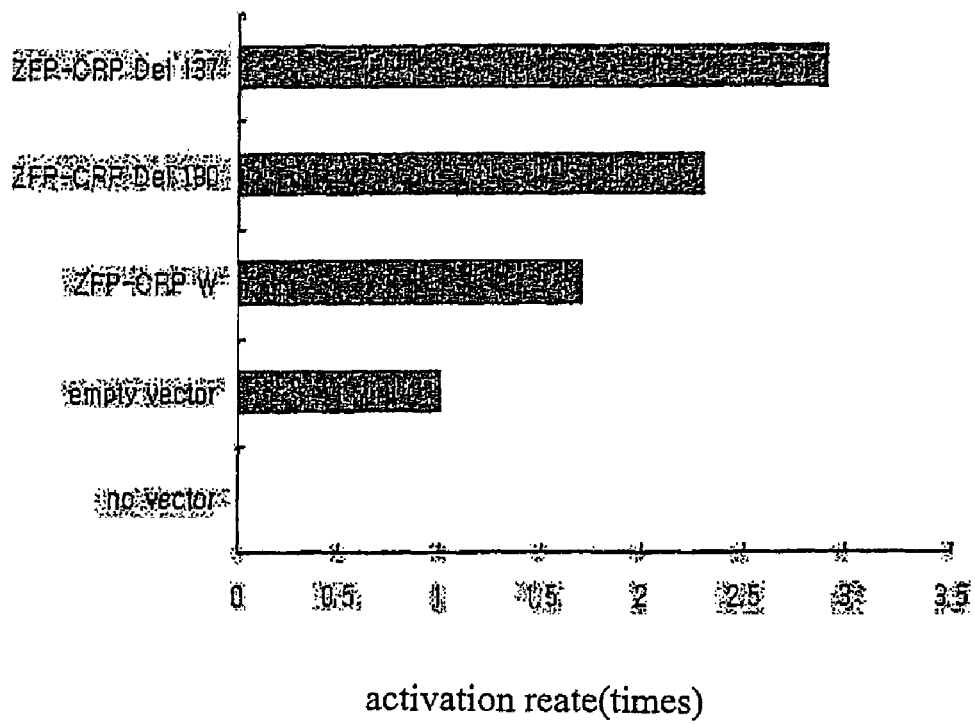
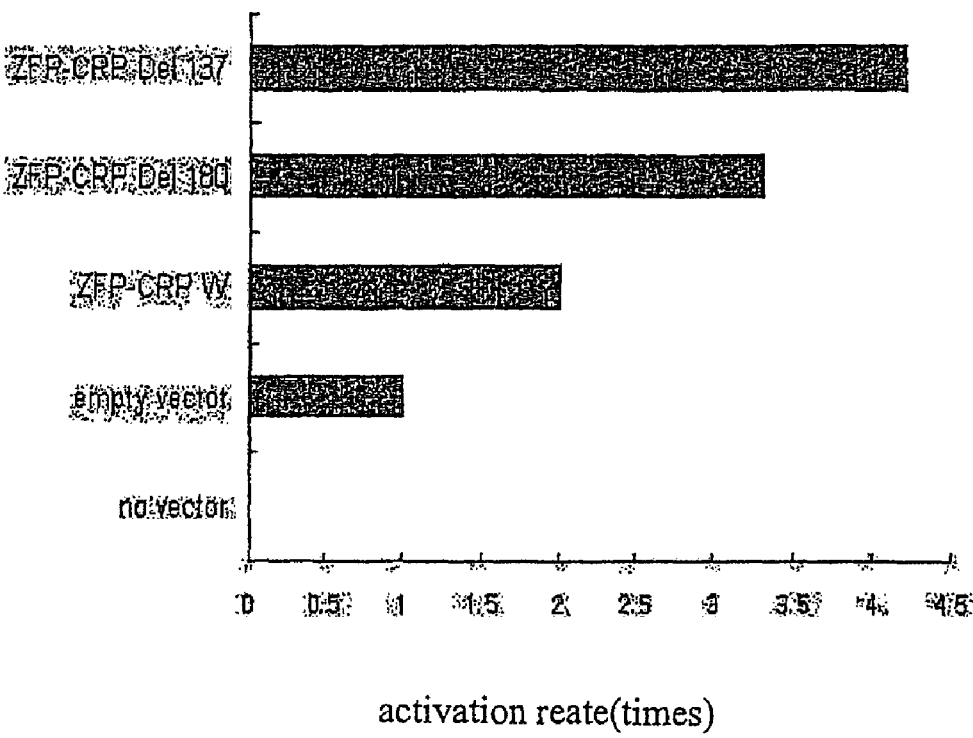

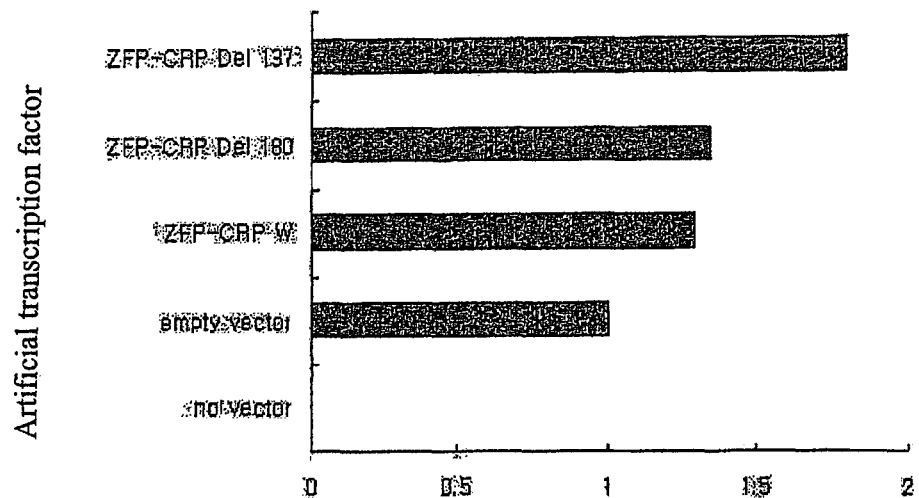
[Fig. 8]
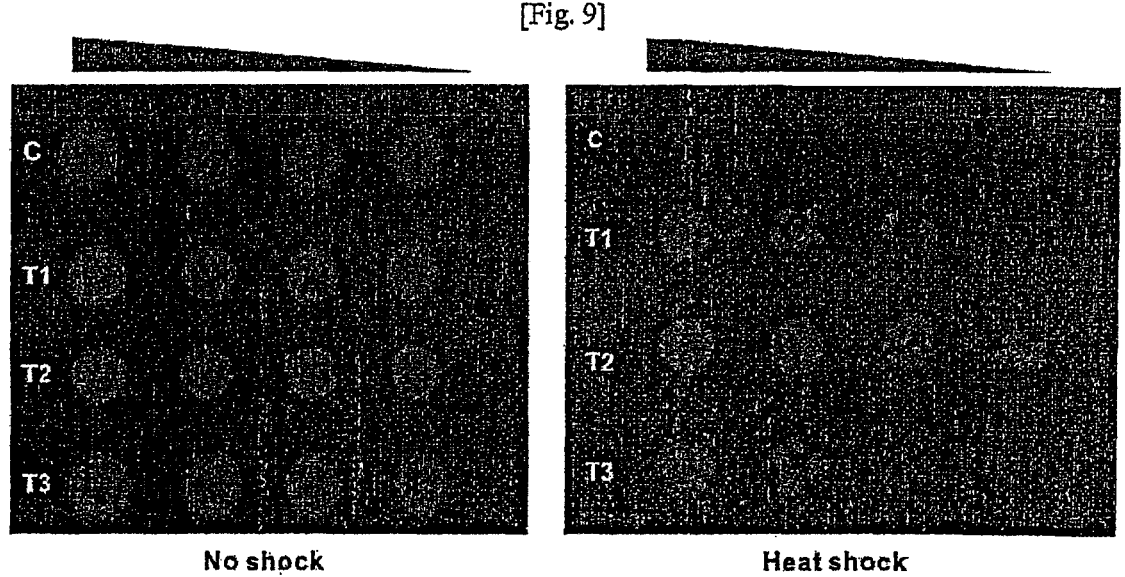
[Fig. 9]

[Fig. 10]
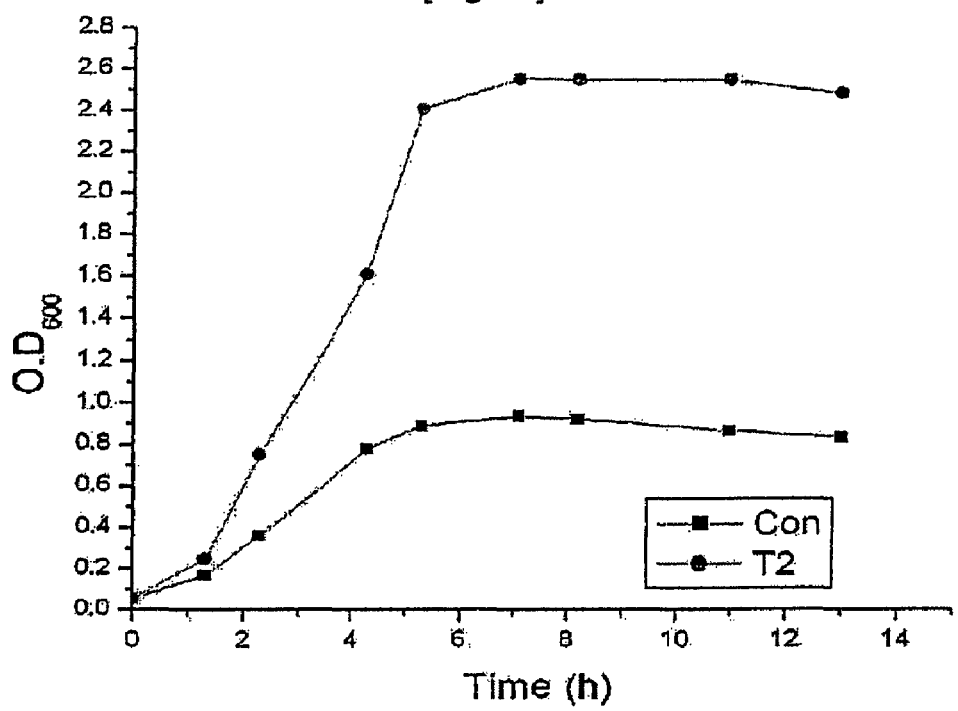
[Fig. 11]
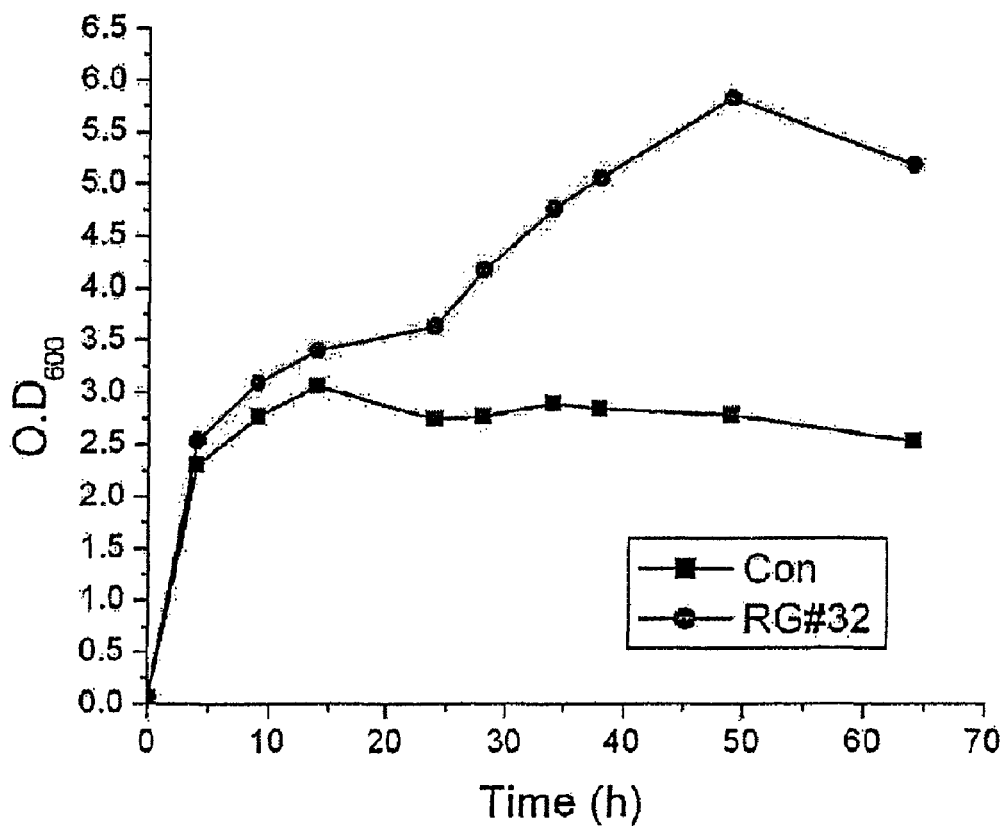

[Fig. 12]
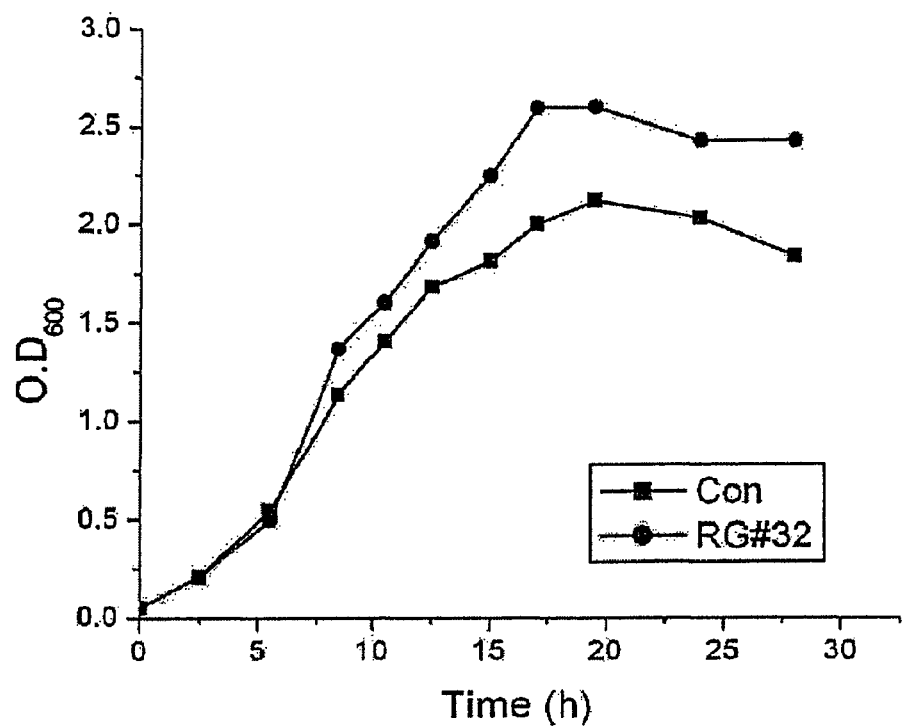
[Fig. 13]
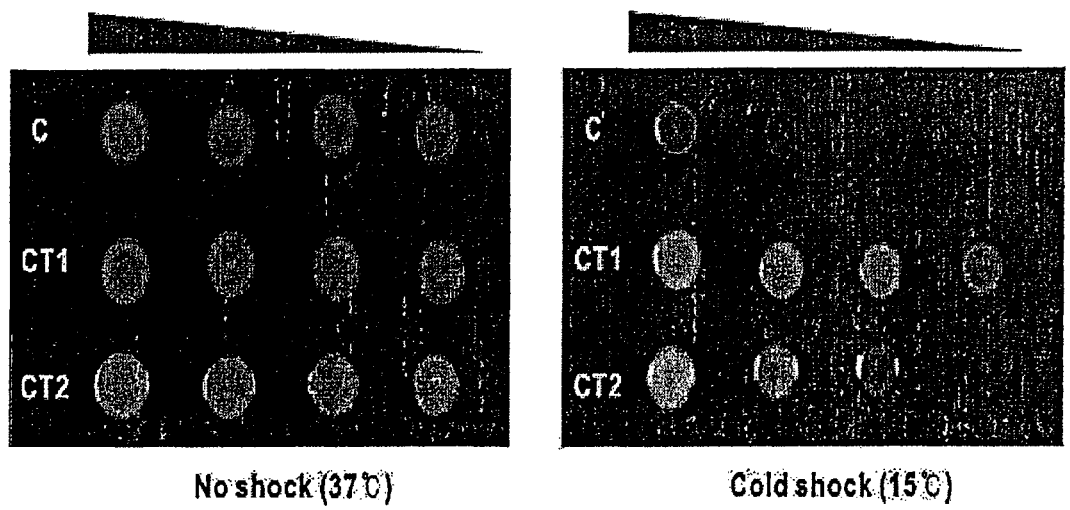
No shock (37°C)　　　　Cold shock (15°C)

[Fig. 14]
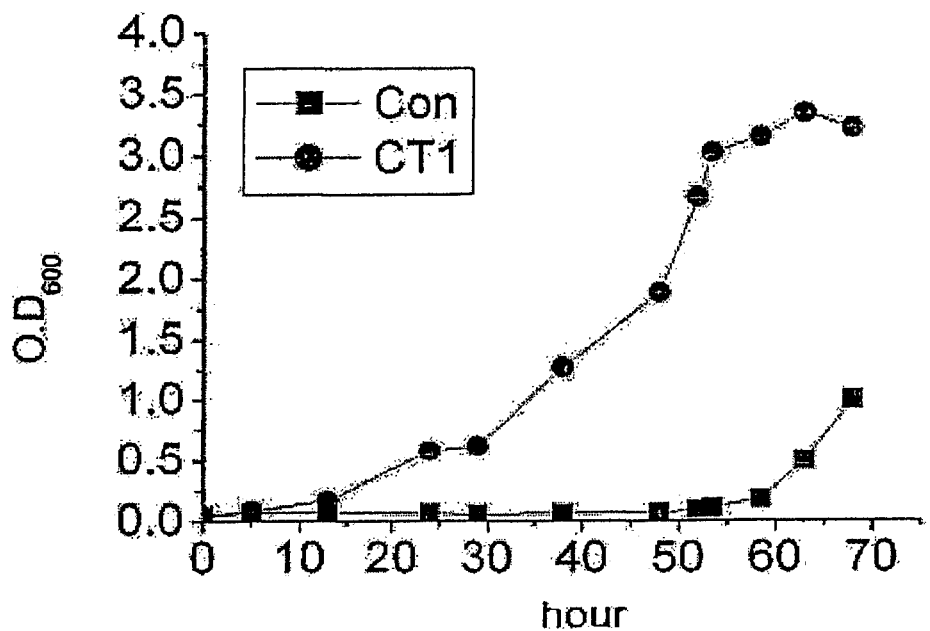
[Fig. 15]
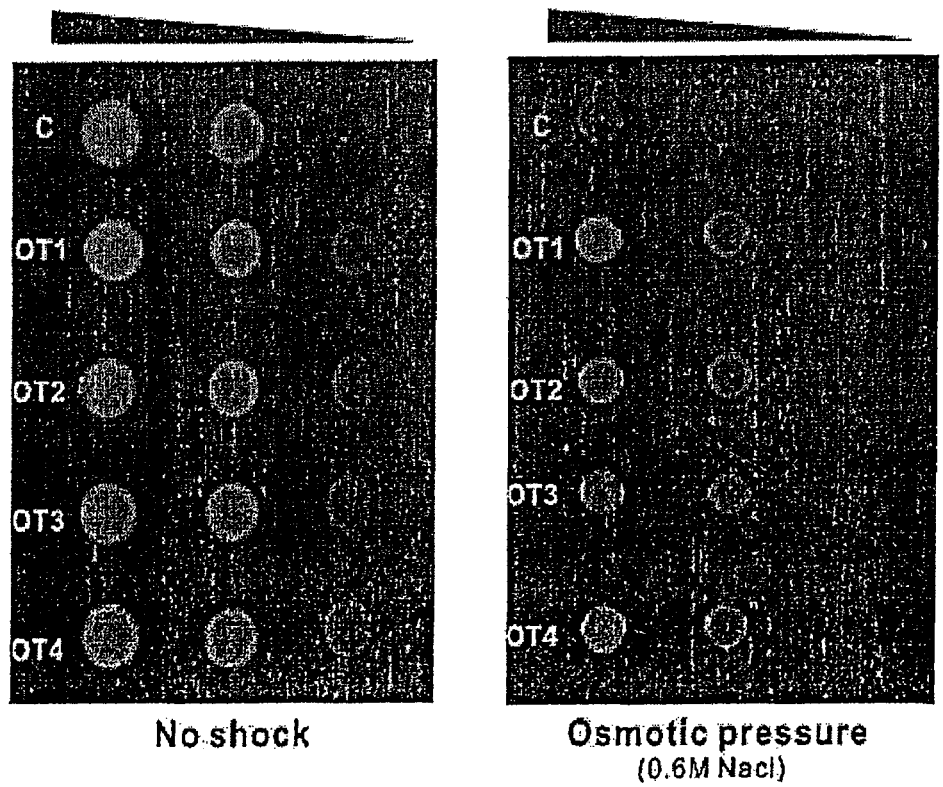
No shock      Osmotic pressure
(0.6M NaCl)

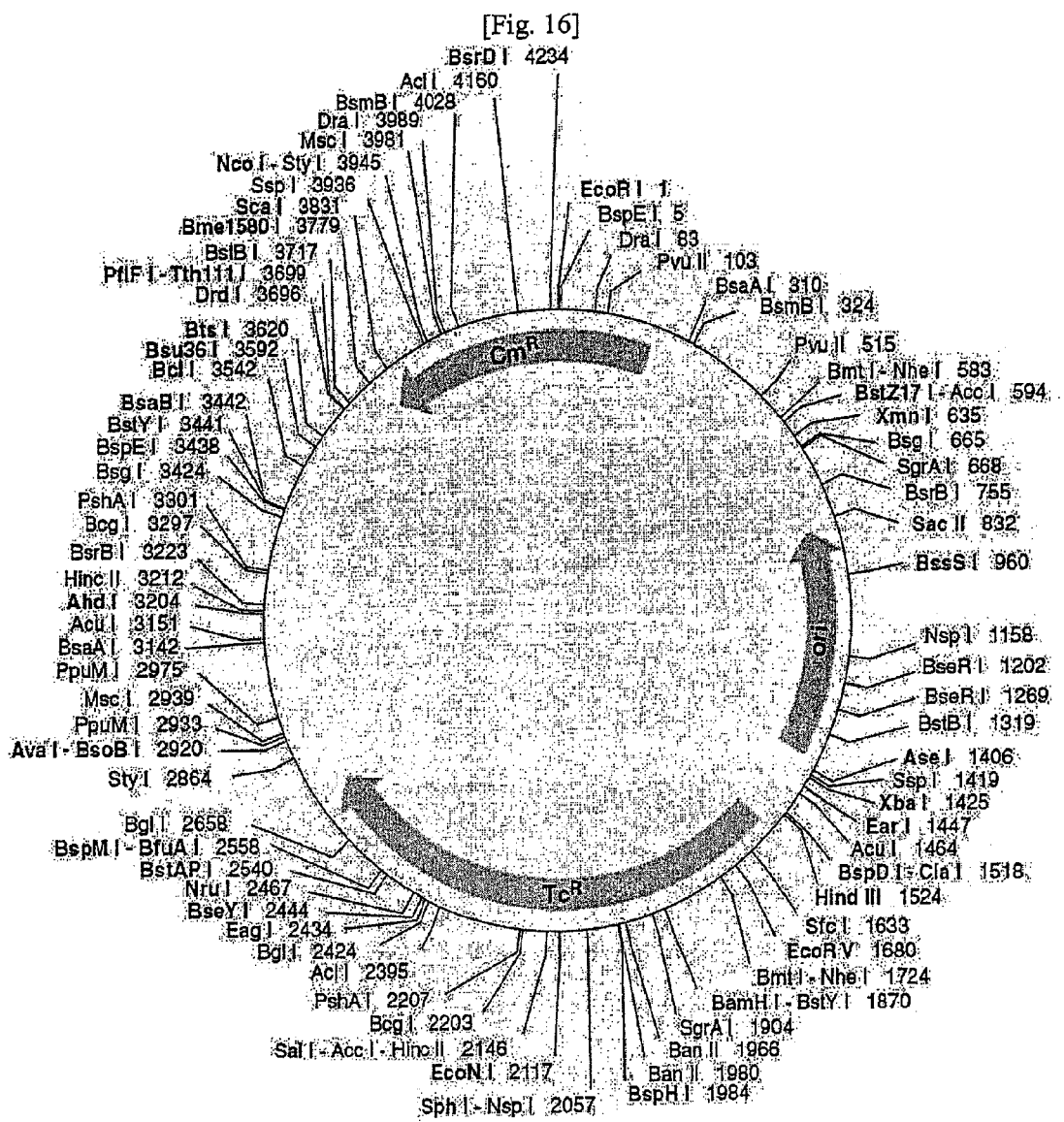
[Fig. 16]

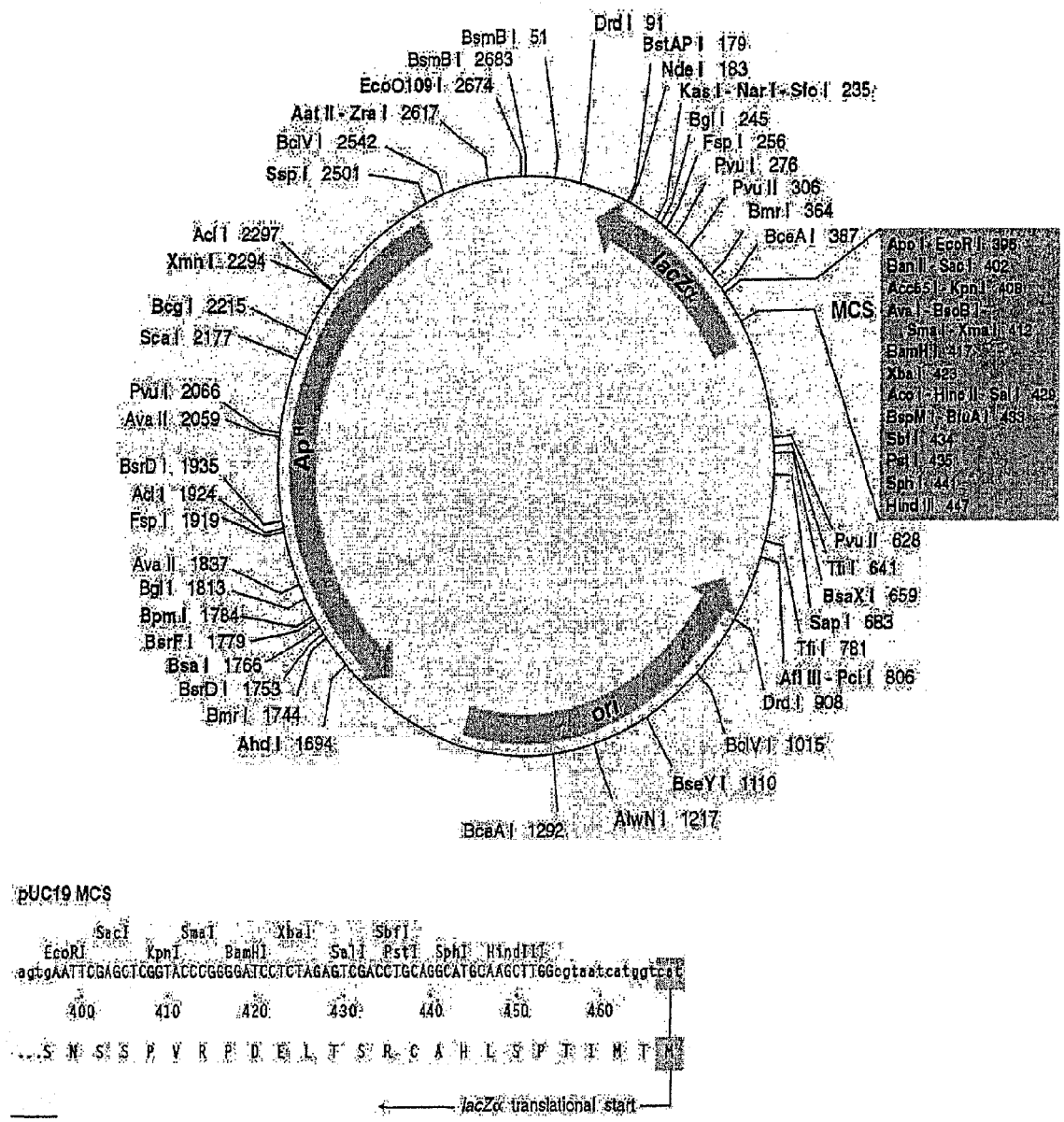
[Fig. 17]

PREPARATION OF AN ARTIFICIAL TRANSCRIPTION FACTOR COMPRISING ZINC FINGER PROTEIN AND TRANSCRIPTION FACTOR OF PROKARYOTE, AND A USE THEREOF

CROSS-REFERENCE TO RELATED APPLICATIONS

This application is the national phase of PCT application PCT/KR2006/005493 having an international filing date of 15 Dec. 2006, which claims benefit of Korean patent application No. 10-2006-0103675 filed 24 Oct. 2006. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 300602006100Seqlist.txt | 22 Jan. 2010 | 37,773 bytes |

BACKGROUND OF THE INVENTION

1. Technical Field

The present invention relates to artificial transcription factors capable of artificially regulating gene expression of *Escherichia coli* by using zinc finger proteins and transcription factors of prokaryote, and engineered *E. coli* using the same.

2. Background Art

With the advent of post-genome age, researches and analyses are being actively ongoing based on gene information of living things (i.e., organisms). Development and the necessity of a system that may artificially regulate the gene expression draw much attention and are one of fields that are being studied most actively. Up- or down-regulating the expression of specific genes in an organism or a cell and analyzing biological results to be obtained therefrom could allow to discover a function of the specific gene or biological role of the gene. In addition, if the expression of a target gene is properly controlled, this can be utilized as a means for a gene therapy. Furthermore, because the phenotypes of the organism are determined by whether the specific gene is expression or the level of the gene expression in the nature, it can be utilized in development of a desired industry microorganism to prepare an organism expressing with desired phenotypes by regulating the gene expression thereof.

It has been recently reported that it is possible that the gene expression is regulated by using zinc finger proteins. The zinc fingers are known as a DNA binding motif of a DNA binding proteins that are most frequently discovered in eukaryote. The zinc fingers are an active domain that can recognize sequence-specifically a target sequence and can work as transcription repressor by themselves. Furthermore, a new transcription factor can be prepared by fusing the zinc finger proteins with a transcription activating (or suppressing) domain, wherein the zinc finger proteins is used as a DNA binding domain.

It has been recently reported that the target gene expression is able to be up- or down-regulated when a sequence-specific zinc finger DNA binding domain are fused with various types of appropriate effector domains (activating domains or suppressing domains) and expressed in the form of the transcription factor in cells (Liu, Q., Segal, D. J., Ghiara, J. B., and Barb as, C. F., III, 1997 *Proc. Natl. Acad, Sci.* U.S.A. 94. 5525-5530; Beerli, R. R., Segal, D. J., Dreier, B., and Barbas C. F., III, 1988, *Proc. Natl. Acad. Sci.* U.S.A. 95, 14628-14633; Beerli R. R., Dreier B. Barbas C.F. 3$^{rd}$, Positive and negative regulation of endogeneous genes by designed transcription factor, *Proc. Natl. Acad. Sci.* USA 2000 Feb. 15: 97(4), 1495-500).

However, in the current research for the procaryotic cells, because only the zinc finger domains are used as the transcription factors without the effector domain, only the effect that the gene expression is suppressed can be obtained, which is, however, very weak. Namely, in order to effectively obtain various phenotypes, it is not only necessary to suppress the gene expression but also to activate the expression of various genes.

Therefore, the inventors of the present disclosure has developed novel artificial transcription factors which can up-regulate the gene expression of *E. coli* as well as down-regulate it by fusing transcription factors of *Escherichia coli*, which is industrially a useful prokaryote, as the effector domain to a zinc finger domain library, and has discovered that gene expression of *E. coli* can be artificially regulated by introducing the novel artificial transcription factors in *Escherichia coli*, and thus engineered *E. coli* having various phenotypes is able to be prepared through experimentations, thus completing the present invention.

DISCLOSURE

Technical Problem

Therefore, in order to address the above matters, the various features described herein have been conceived.

An object of the present invention is to provide a preparation for artificial transcription factors that can artificially up- or down-regulate the gene expression by fusing zinc finger domains to transcription factors of prokaryotes as an effector domain, and also provide an engineered *E. coli* having various phenotype specificities.

Technical Solution

To achieve the above object, there is provided artificial transcription factors which is able to artificially up- or down-regulate the gene expression, wherein the artificial transcription factors comprising one to three zinc finger domains and a transcription factor of prokaryotes as an effector domain. Said transcription factor of prokaryotes used as an effector domain may be CRPs (Catabolite regulatory proteins) (or cyclic AMP receptor proteins) or its derivatives, such as a wild type CRP (CRP W, residue 1-209), CRP Del 137 (residue 137-190), or CRP Del 180 (residue 1-180).

In one embodiment, the zinc finger domains may be identified from human genes and selected from the group consisting of nucleic acid sequences having SEQ ID NOs. 13 to 64.

In another embodiment, the present invention provides a reporter plasmid in which the gene encoding enhanced green fluorescent protein (EGFP) was used as a reporter to select the most potent effector domains. Two different reporter plasmids were constructed by inserting the target DNA sequences for the artificial transcription factors into two different parts of the reporter gene. Specifically, the resulting plasmids were pEGFP-A, which contained the artificial transcription factor target sequence upstream of the reporter promoter (−67 to −50), and pEGFP-R, which contained the artificial transcription factor target sequence downstream of the promoter (+24 to +41).

In further embodiment, the present invention provides an engineered E. coli having various phenotypes by introducing the artificial transcription factor thereto, such as E. coli having the resistance to heat or cold shock, E. coli having the improvement of growth, and E. coli having the resistance to osmotic pressure. The present invention will now be described in detail.

DNA Binding Domain—Zinc Finger Domain

A zinc finger domain is a DNA binding motif of DNA binding proteins that are most frequently discovered in eukaryotes, which is discovered in various species from yeast to higher plant life and human beings. The zinc finger domain has been known to function as a transcription repressor that down-regulate the gene expression by itself. Therefore, if fusing the zinc finger domain with the effector domain (up- or down-regulation), the resulted fusing protein, which is a novel transcription factor, may up- or down-regulate the expression of a target gene that is recognized by the zinc finger.

In the present disclosure, the zinc finger domain may be a Cys2-His2 type, which three or more zinc finger domains are arranged in parallel to constitute a zing finger protein. Because a single zinc finger domain can recognize a target sequence comprising three or four bases, it can prepare a sequence-specific zinc finger that can selectively recognize target sequences of 9-10 bases by properly re-arranging and linking several zinc finger domains each other.

In the present disclosure, one to three zinc finger domains of human genome are arranged to be used as a DNA binding domain of newly developed transcription factors of the present invention. Preferably, the zinc finger domains of the present invention are identified from the human genome. In order to confirm the function of the effector domain of the novel transcription factors, in the present disclosure, it is prepared and used an experimental zinc finger protein that can recognize 5'-GCG GCG GGG-3' sequence on a reporter plasmid as a target. Preferably, experimental transcription factors comprising effector domain and three zinc finger proteins (ZFP2, ZFP1, and ZFP1, ordered in the N- to C-terminal direction) were prepared by using ZFP1 recognizing 5'-GCG-3' and ZFP2 recognizing 5'-GGG-3' as zinc fingers, and used.

An Effector Domain

In general, the transcription factors of prokaryotes simultaneously have two functions of activating and repressing transcription. It depends on a position on a genomic sequence in which transcription factors are bound whether transcription is activated or repressed. In general, it is known that when the transcription factors are bound to a portion in range of −80 to −30 starting from a transcription start point, the gene expression is activated, and when the transcription factors are bound to a portion lower than −30 starting from a transcription start point, the gene expression is repressed.

The present invention is directed to development of transcription factors to be operable in Escherichia coli, the prokaryote. While in case of the eukaryotes different domains are needed for each of transcription activation and repression, in case of the transcription factors of the present invention it may be simultaneously accomplished two functions of activating and repressing transcription by using a single effector domain with good activity.

In addition, only a transcription activating domain within the transcription factors that substantially repress or activate the gene expression as well as the wild type transcription factors can be used as the effector domain.

In the present disclosure, the transcription factors of the procaryotic cell may be used as the effector domain. Preferably, the CRP (catabolite regulatory protein, cyclic AMP receptor protein), which is a typical transcription factor of the Escherichia coli, and its derivative may be used as the effector domain. The CRP is widely known as a transcription factor that regulates gene expression at over 100 promoters in the Escherichia coli. The CRP comprises 209 amino acids and consists of two domains. Namely, the CRP includes an N-terminal domain that is responsible for interaction between dimerization of the CRP and c-AMP and a C-terminal domain that is responsible for interaction with DNA. Furthermore, the CRP includes three types of activating domains for transcription activation, such as AR1 (residue 156-164), AR2 (residue 19, 21, 96 and 101), and AR3 (residue 52, 53, 54, 55, 58). Especially, AR1 is the most favored activating domain in the transcription activation (Busby, S., Ebright, R. H., *J Mol Biol*, 293, 1999, 199-213; Rhodius, V. A., West, D. M., Webster, C. L., Busby, S. J., Savery N., *J. Nucleic Acids Res.*, 25, 326-332, 1997; Rhodius, V. A., Busby, S. J., *J. Mol. Biol.*, 299, 295-310, 2000; Wagner, R., Transcription regulation in prokaryotes., 199-207 and 211-217. Oxford University Press, Oxford, 2000).

In the present invention, because the zinc finger domain is used as the

DNA binding domain and the CRP is needed only to work as the effector domain. Namely, the DNA binding domain of the CRP is not needed. Thus, the CRP derivatives may be used as the effector domain, wherein the CRP derivatives including the CRP being removed the DNA binding domain or comprising the AR1 region. Preferably, the three following types can be used as the effector domain: CRP W (residue 1-209) as the wild-type CRP, CRP Del 137 (residue 137-190), and CRP Del 180 (residue 1-180) as the CRP derivative.

A Peptide Linker

Various linkers may be used to link the DNA binding domains to each other or link the DNA binding domains with the effector domain. In the present disclosure, it may use a linker that links the zinc finger domains in naturally occurring zinc finger proteins. A typically naturally occurring linker is Thr-Gly-(Glu-Gln)-(Lys-Arg)-Pro-(Tyr-Phe) (SEQ ID NO:65). In the present invention, Thr-Gly-Glu-Lys-Pro-Tyr (SEQ ID NO:66) can be used to link the zinc finger domains to each other or link the zinc finger domains to the effector domain.

A Reporter Plasmid

In the present invention, it is prepared for two types of reporter plasmids in order to test the gene expression capability of the artificial transcription factor, wherein the two types of reporter plasmids are pEGFP-A for testing the activation of the gene expression and pEGFP-R for testing the repression of gene expression. Each of reporter plasmid were modified by using tac promoter controlled by lacI which is endogenous transcription factor in E. coli in order to test whether or not the transcription factors of the present invention affect. Said modification of tac promoter was introduced by inserting a sequence of 5'-GCG GCG GGG-3,' which the transcription factor of the present invention may target and bind, into adjacent region of tac promoter in each of reporter plasmid. Namely, said reporter plasmids were prepared by inserting binding sequence of the test transcription factor into proper region starting from the transcription start point because as aforementioned, it depends on binding position starting from the transcription start point whether the prokaryotic transcription factor activates or represses the gene expression.

In one embodiment, in order to demonstrate the gene expression activation capability of test transcription factor, the reporter plasmid is prepared by means of inserting two copies of 5'-GCG GCG GGG-3' into a region in range of −67 to −50 starting from the transcription start point. In order to demonstrate the gene expression repression capability of test transcription factor, the reporter plasmid is prepared by means of inserting two copies of 5'-GCG GCG GGG-3' into a region in range of +24 to +50 starting from the transcription start point as shown in FIG. 3.

GFP derivatives (Clontech Laboratories, Inc., Calif.) may be used as the reporter gene, because they have improved green fluorescent characteristics that facilitate identification and quantitativeness of the gene expression. The expression of the GFP derivatives can be detected by measuring fluorescent emission upon being excited with confocal microscopy or spectrofluorometer.

Advantageous Effects

The present invention relates to artificial transcription factors comprising zinc finger domain and catabolite regulatory proteins derived from the prokaryote used as the effector domain. Although the zinc finger domain of the present invention derives from the eukaryote, it can be also activated in the prokaryote. Furthermore, the artificial transcription factors of the present invention can regulate activation of various prokaryotes because it has the catabolite regulatory proteins derived from various prokaryotes as an effector domain. In detail, if the transcription factors of the present invention are introduced, the gene expression can be activated or repressed regardless operation of the endogenous transcription factors in *E. coli*. Such fact can be used for inducing various *E. coli* having phenotypes desired by the user, or for analyzing the currently unknown function of gene, or for inducing the *E. coli* having desired useful characteristics, such as the resistance heat or cold shock, or osmotic pressure or the improvement of growth. Therefore, the present invention can be used in various industries.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 is a scheme showing phenotypic engineering of *E. coli* by using an artificial transcription factor, in which circles represent zing finger domains and squares represent effector domains;

FIG. 2 is a scheme showing zing finger proteins used for test transcription factors which are prepared for demonstrating a function of catabolite regulatory protein (or cyclic AMP receptor protein (CRP)) of *E. coli* and their sequence, in which sequences recognized by the respective zinc finger proteins are shown below the zinc fingers.

FIGS. 3 and 4 illustrate fragments of reporter plasmids which are prepared by inserting specific sequence recognized by zinc finger protein of test transcription factor in FIG. 2 into up or down stream of tac promoter in order to demonstrate the function of the CRP as the effector domains of the artificial transcription factor, wherein FIG. 3 shows a reporter plasmid pEGPF-A for demonstrating gene expression activation capability of the artificial transcription factors and FIG. 4 shows a reporter plasmid pEGFP-R for demonstrating gene expression repression capability of the artificial transcription factors;

FIG. 5 shows photos illustrating that the test transcription factor activates the transcription of GFP derivatives (EGFP) reporter gene having improved green fluorescent characteristics of the pEGFP-A, as obtained by a confocal microscopy;

FIG. 6 is a graph showing numerically activation degrees of the activated reporter gene expression by the test transcription factors in FIG. 5;

FIG. 7 is a graph showing numerically activation degrees of the repressed reporter gene by the experimental transcription factors in FIG. 5;

FIG. 8 is a graph showing numerical repression degrees of the activated reporter gene, by the test transcription factors;

FIG. 9 shows photos of *E. coli* having the resistance to heat shock, which is selected by the artificial transcription factors prepared by using CRP Del 180 as an effector domain;

FIG. 10 is a graph showing a growth curve of T2, which is an *E. coli* having the highest resistance to heat shock, at 50° C.;

FIG. 11 is a graph showing a growth curve of *Escherichia coli*, which grows better through the artificial transcription factors prepared by using CRP Del 180 as the effector domain, at 37° C. and LB medium;

FIG. 12 is a graph showing a growth curve of *Escherichia coli*, which grows better through the artificial transcription factors prepared by using CRP Del 180 as the effector domain, at 37° C. and M9 medium;

FIG. 13 shows photos of *E. coli* having the resistance to cold shock, which is selected by the artificial transcription factors prepared by using CRIP Del 180 as the effector domain;

FIG. 14 is a graph showing a growth curve of CTI, the *E. coli* having the highest resistance to cold shock, and that of a control;

FIG. 15 show photos of *E. coli* having the resistance to osmotic pressure, which is selected by the artificial transcription factors prepared by using CRP Del 180 as the effector domain;

FIG. 16 shows a cleavage map of pACYC184 plasmid; and

FIG. 17 shows a cleavage map of pUC19 plasmid.

MODE FOR INVENTION

The present invention will now be described in detail through the following embodiments and experimentations. The following embodiments and experimentations are exemplary cases and the scope of the present invention is not limited thereto.

Embodiment 1

Preparation of Test Transcription Factors

For demonstrating the function of a transcription factor according to the present invention, test zinc finger domains that can recognize 5'-GCG GCG GGG-3' sequence on a reporter plasmid as a target were prepared by using the following zinc finger domain: ZFP1 recognizing 5'-GCG-3' and ZFP2 recognizing 5'-GGG-3'. CRP W (sequence No. 1), CRP derivative CRP Del 137 (residue 137-190, sequence No. 3) and CRP Del 180 (residue 1-180, sequence No. 5) were used as an effector domain. Three test transcription factors were prepared using said 3 CRP: ZFP-CRP W, ZFP-CRP Del 180 and ZFP-CRP Del 137 using CRP W, CRP Del 180 and CRP Del 137 as the effector domain, respectively. Said transcription factors comprise the effector domain-ZFP2-ZFP1-ZFP1 from N-terminal to C-terminal (see FIG. 2).

The effector domains were isolated from the *E. coli* and amplified using PCR, followed by cloning to an expression plasmid by using NcoI and EcoRI. Thereafter, each of the synthesized zinc finger domains was linked to the expression plasmid in which the effector domains were cut with AgeI and EcoRi by using XmaI and EcoRI orderly.

In addition, the ZFP1, the zinc fingers of the test transcription factors, were selected from human genome sequence, and encoded by human nucleic acid sequence of SEQ ID NO. 9. Furthermore, ZFP2, the zinc filter of the experimental transcription factors was also selected from the human genome sequence and encoded by human nucleic acid sequence of SEQ ID NO. 11.

Embodiment 2

Preparation of Reporter Plasmids

Reporter plasmids, which are used for confirmation of activating or repressing the gene expression, were prepared by modifying pACYC184 (New England Biolabs, Inc., USA as shown in FIG. 16). The reporter plasmids were prepared by amplifying GFP derivative (EGFP) gene having improved green fluorescent characteristics as a reporter gene, a tac promoter gene, and a target sequence of a test transcription regulatory factor with PCR and inserting them to pACYC184. The pEGFP-A, the reporter plasmid for observing gene expression activation, was prepared by inserting two copies of 5'-GCG GCG GGG-3' to a region in range from −67 to −50 starting from a transcription start point (see FIG. 3). Furthermore, the promoter of pEGFP-R as the reporter plasmid for observing gene expression repression capabilities of the test transcription factors was prepared by inserting two copies of 5'-GCG GCG GGG-3', the target sequence of the test transcription factors into a region in range from +24 to +41 starting from the transcription start point (see FIG. 4). SEQ ID NO. 7 is the nucleic acid sequence of the pEGFP-A reporter plasmid, and SEQ ID NO. 8 is the nucleic acid sequence of the pEGFP-R reporter plasmid.

Experimental Example 1

Checking Function of Effector Domains

It is observed through the following experiments whether the transcription factors according to the present invention can artificially activate or repress the gene expression without being affected by lacI repressor, the endogenous transcription factors in *E. coli* (*E. coli* MG1655 K-12 Blattner laboratory).

For observing the activation of the gene expression, inserting the test transcription factors, i.e. ZFP-CRP W, ZFP-CRP Del 180 and ZFP-CRP Del 137 prepared in the embodiment 1 into the pEGFP-A reporter plasmid prepared in the embodiment 2

It was performed to insert the test transcription factors, i.e. ZFP-CRP W, ZFP-CRP Del 180 and ZFP-CRP Del 137 prepared in Embodiment 1 into the p EGFP-A reporter plasmid for observing the activation of the gene expression and into the pEGFP-R reporter plasmid for observing the repression of the gene expression, wherein said reporter plasmids were prepared in Embodiment 2, and then to observe whether the expression of the reporter gene is activated or repressed by test transcription factors when adding 1 mM IPTG (Isopropyl-β-D-thiogalactopyranoside) or not. Such expression of the reporter gene was detected by a level of fluorescence with the confocal microscopy. This detection of fluorescence can be due to the GFP derivative gene having the green fluorescent characteristics in the reporter plasmid.

In addition, an activation degree or a repression degree of the reporter gene expression by the test transcription factors according to the present invention was obtained. Specifically, in order to obtain the activation degree, an amount of reporter gene expression in a cell in which a plasmid that encodes the test transcription factors had been introduced was divided by an amount of reporter gene expression obtained from cell in which the control plasmid that does not encode the test transcription factors prepared in embodiment 1 were introduced. Meanwhile, in order to obtain the repression degree, an amount of reporter gene expression obtained from cell in which the control plasmid that does not encode the test transcription factors prepared in embodiment 1 were introduced was divided by an amount of reporter gene expression in a cell in which a plasmid that encodes the test transcription factors had been introduced.

The above experimental results are as shown in FIG. 5. 'No vector' in FIG. 5 means wild type *E. coli* in which the reporter plasmid and the plasmid encoding the test transcription factors have not been introduced, and 'empty vector' means an *E. coli* in which the reporter plasmid and the plasmid noncoding the test transcription factors. ZFP-CRP W refers to an *E. coli* in which the reporter plasmid and a plasmid encoding the test transcription factors fused with the wild type CRP as the effector domain are introduced, ZFP-CRP Del 180 refers to an *E. coli* in which the reporter plasmid and a plasmid encoding the test transcription factors fused with the CRP residue 1-180, one of the CRP derivatives, as the effector domain are introduced, and ZFP-CRP Del 137 refers to an *E. coli* in which the reporter plasmid and a plasmid encoding the test transcription factors fused with the CRP residue 137-190, one of the CRP derivatives, as the effector domain are introduced.

As shown in FIG. 5, it was demonstrated that the test transcription factors having the CRP derivatives, such as CRP Del 180 and CRP Del 137, as the effector domains better activate the expression of the reporter genes compared with the wile type CRP W. In addition, it was observed that test transcription factors enhance the activation of the expression of the reporter genes which have been already activated by IPTG, such that ZFP-CRP Del 180 and the ZFP-CRP Del 137 activates the expression of the EGFP by twice and three times, respectively (see FIGS. 5A to 5E and FIG. 6).

Furthermore, it was demonstrated that the test transcription factors according to the present invention activate the expression of the reporter genes of pEGFP-A which had been repressed by not adding IPTG, and that ZFP-CRP W, ZFP-CRP Del 180 and ZFP-CRP Del 137 activated the expression of the EGFP by twice, three and four times, respectively (see FIGS. 5F to 5J and FIG. 7).

Meanwhile, regarding repression of the reporter genes, as shown in FIG. 8, it was confirmed that the test transcription factors repress the expression of the reporter gene which have been already activated by IPTG in pEGFP-R, and that ZFP- CRP Del 180 and ZFP-CRP Del 137 repress the expression of the reporter genes by 1.5 times and twice, respectively.

Accordingly, to sum up the experimentation results, the test transcription factors according to the present invention can effectively regulate the expression of the reporter genes regardless of lacI proteins which are the endogenous transcription repressor in the *Escherichia coli*.

Experimental Example 2

Preparation of Transcription Factor Library 26 types of zinc finger domains of human genomes selected from GenBank database search results were synthesized and cloned into pUC19 (New England Biolabs. Inc., USA, Refer to FIG. 17). Two different transcription factor libraries were prepared by cloning and fusing CRP Del 137 and CRP Del 180 as the effector domain into transcription factor expression plasmid, respectively. The preparation of the transcription factor libraries were made in the same manner as the method for preparation of the experimental transcription factor. This is, the expression plasmid in which the effector domains were cloned was cut with AgeI and EcoRI. pUC19 in which different zinc finger domains were cloned were mixed by the same amount and cut with XmaI and EcoRI. The expression plasmid cloning the effector domain which was cut with AgeI and EcoRI and the zinc finger domains which was cut with XmaI and EcoRI were ligated to prepare a library comprising the effector domain and a single zinc finger domain. Thereafter, in the same manner above, the expression plasmid in which the effector domain and a single zinc finger domain were cloned was cut with AgeI and EcoRI and then ligated with the zinc finger domain which was cut with XmaI and EcoRI to connect the second zinc finger domain. And finally, the transcription factor library comprising the three zinc finger domains and the effector domain were prepared in the same manner above.

Following is 26 types of zinc finger domains, Z1 to Z26, selected from the human genomes sequences resulted from searching the GenBank database:

Z1 is encoded by nucleic acid sequence of SEQ ID No. 13;
Z2 is encoded by nucleic acid sequence of SEQ ID No. 15;
Z3 is encoded by nucleic acid sequence of SEQ ID No. 17;
Z4 is encoded by nucleic acid sequence of SEQ ID No. 19;
Z5 is encoded by nucleic acid sequence of SEQ ID No. 21;
Z6 is encoded by nucleic acid sequence of SEQ ID No. 23;
Z7 is encoded by nucleic acid sequence of SEQ ID No. 25;
Z8 is encoded by nucleic acid sequence of SEQ ID No. 27;
Z9 is encoded by nucleic acid sequence of SEQ ID No. 29;
Z10 is encoded by nucleic acid sequence of SEQ ID No. 31;
Z11 is encoded by nucleic acid sequence of SEQ ID No. 33;
Z12 is encoded by nucleic acid sequence of SEQ ID No. 35;
Z13 is encoded by nucleic acid sequence of SEQ ID No. 37;
Z14 is encoded by nucleic acid sequence of SEQ ID No. 39;
Z15 is encoded by nucleic acid sequence of SEQ ID No. 41;
Z16 is encoded by nucleic acid sequence of SEQ ID No. 43;
Z17 is encoded by nucleic acid sequence of SEQ ID No. 45;
Z18 is encoded by nucleic acid sequence of SEQ ID No. 47;
Z19 is encoded by nucleic acid sequence of SEQ ID No. 49;
Z20 is encoded by nucleic acid sequence of SEQ ID No. 51;
Z21 is encoded by nucleic acid sequence of SEQ ID No. 53;
Z22 is encoded by nucleic acid sequence of SEQ ID No. 55;
Z23 is encoded by nucleic acid sequence of SEQ ID No. 57;
Z24 is encoded by nucleic acid sequence of SEQ ID No. 59;
Z25 is encoded by nucleic acid sequence of SEQ ID No. 61;
Z26 is encoded by nucleic acid sequence of SEQ ID No. 63.

Experimental Example 3

Induction of Various Transformed *E. Coli* by Using Novel Transcription Factors

*E. coli* having desired phenotypes under particular condition was induced and selected by introducing the transcription factor library prepared in experimental example 2 into *E. coli*. Transcription factors were isolated from the *E. coli* having the desired phenotypes, and re-transformed to the *E. coli* to confirm whether the same phenotypes were induced to thus confirm the induction of the particular phenotypes by the transcription factors.

3-1. Induction of *E. Coil* Having the Resistance to Heat Shock

A large amount of expression of heterologous proteins at a high temperature increases their solubility. Thus, understanding of heat shock response in the *E. coli* can be an important issue for development of an industrial microorganism. In one embodiment, after the transcription factor library was introduced into the *Escherichia coli*, an *E. coli* having artificial transcription factors comprising CRP Del 180 as the effector domain was thermally shocked during two hours at 55° C., and plated on an LB plate, and then cultivated at 37° C. After that, an *E. coli* having heat resistance was selected from colonies which had been grown from the cultivation.

Transcription factors were isolated from the selected *E. coli* and confirmed through DNA sequence analysis, which were then re-transformed into the *E. coli* in order to confirm whether their heat resistance was induced, thus confirming activity of the transcription factors. Observing a growth pattern of the *E. coli* at 100 ml LB medium at 50° C., samples of the *E. coli* were taken at intervals of about one hour and half minutes to measure optical density (OD) at spectrophotometer 600 nm to obtain a growth curve of the *Escherichia coli*.

FIG. 9 shows the results of the experimentation. The left photo in FIG. 9 is a photo of a control of the *E. coli* to which heat shock was not applied, while the right photo shows a survivality of the *E. coli* after heat shock was applied for 2 hours at 55° C. 'C' in the photos indicates control *E. coli* having control plasmid in which artificial transcription factors were not encoded, while T1 to T3 indicate *E. coli* having heat resistance by different artificial transcription factors. As shown in FIG. 9, under the conditions in which no heat shock was applied, every *E. coli* formed colonies, while under the conditions in which the heat shock was applied, growth of the wild-type *E. coli* was hampered but the *E. coli* having the transcription factors comprising CRP Del 180 as the effector domains according to the present invention grew well even with the heat shock. The triangles at upper portions in FIG. 9 indicate a 5× diluted cell density.

Among them, the transcription factors of T2 were checked to have grown most satisfactorily, whose growth curve at 50° C. is shown in FIG. 10. The transcription factors of T2 having the highest heat resistance are as follows:

T1=CRP 1~180a.a+Z23+Z11+Z19

T2=CRP 1~180a.a+Z13+Z2+Z23

T3=CRP 1~180a.a+Z9+Z4+Z11

3-2. Induction of Transformed *E. coli* with Improved Growth Speed

Because fast growth speed of a host cell increases the productivity, it is very useful in the industrial fields. Accordingly, in the present invention, CRP Del 180 is used as the effector domain, and the transcription factor library prepared in experimentation example 2 was introduced to induce *E. coli* having the improved growth rate at 37° C., an optimal growth temperature and be screened.

After introducing the transcription factor library to the *Escherichia coli*, it was subcultured (transferred 1 ml by 1 ml to a new 100 ml medium at intervals of 24 hours during seven days) at 37° C. at the LB medium and M9 medium of 100 ml, streaked or diluted, and then plated to obtain colonies. A growth pattern of each colony was checked at the LB medium and M9 medium of 100 ml at 37° C. and *E. coli* having improved growth rate was finally selected. Transcription factors of the selected *E. coli* was isolated and checked if they are transcription factors through DNA sequence analysis, which is then re-transformed into *E. coli* to confirm whether the growth rate has been improved, thereby confirming the improvement of the growth rate by the transcription factors.

The results of the experimentation are as shown in FIGS. 11 and 12. FIG. 11 shows the results obtained by checking the growth rate at the LB medium at 37° C. and FIG. 12 shows the results obtained by checking the growth speed at M9 medium at 37° C. 'C' indicates control *E. coli* having the control plasmid in which the artificial transcription factors were not encoded, and RG#32 indicates *E. coli* having improved growth rate by the artificial transcription factors. As shown in FIG. 11, in case of the *E. coli* in which the artificial transcription factors were not encoded, its growth rate was not increased after 15 hours of its cultivation, while in case of the *E. coli* having the transcription factors according to the present invention, it were grown continuously until 50 hours after its cultivation. Accordingly, it have been demonstrated that the productivity of the *E. coli* was remarkably improved.

RG#32=CRP1-180a.a+Z26+Z7

As mentioned above, it was confirmed that the zinc finger proteins, the DNA binding domains of the artificial transcription factors in the present invention, can have activation in the prokaryote as well as in the eukaryote. In addition, because the CRP used as the effector domain of the artificial transcription factors has the same sequence with that of CRP of *Shigella* and its family proteins exist in various prokaryotes, it has been estimated that the artificial transcription factors according to the present invention can regulate the gene expression of various prokaryotes as well as *E. coli* and induce various phenotypes thereof.

3-3. Induction of *E. Coli* Having the Resistance to Cold Shock

Because over-expression of target proteins at a low temperature increases solubility and stability of the proteins, an *E. coli* having the resistance to a low temperature may be grown well, which have a high value as an industrial microorganism. Therefore, in order to induce a *E. coli* having resistance to cold shock, the following experimentation was performed. In this experimentation, CRP Del 180 was used as the effector domain, and the transcription factor library prepared in the experimentation example 2 was introduced to induce an *E. coli* that can be grown at a low temperature and be screened.

After introducing the transcription factor library obtained in Experimental Example 2 to the *Escherichia coli*, XL1-Blue (Sambrook and Russel, 2001), it was plated on the LB plate, and cultivated at 15° C. Thereafter, an *E. coli* having resistance to a low temperature (cold shock) was selected. Transcription factors were isolated from the selected *E. coli* and checked through the DNA sequence analysis, which was then re-transformed into *E. coli* to check whether its resistance to the low temperature was induced, thus confirming activity of the transcription factors.

Observing a growth pattern of the *E. coli* at 100 ml LB medium at 15° C., samples of the *E. coli* were taken at intervals of about five hours to measure optical density (OD) at spectrophotometer 600 nm to obtain a growth curve of the *Escherichia coli*. A growth pattern of an *E. coli* was observed at 37° C., the optimum growth temperature, at the 100 ml LB medium as a control.

FIG. 13 shows the results of the experimentation, in which 'C' in the photos indicates control *E. coli* having control plasmid in which artificial transcription factors were not encoded, while CT1 and CT2 indicate *E. coli* having the resistance to a low temperature (cold shock) inducted by different artificial transcription factors. Triangles at upper portions in FIG. 13 indicate a 5× diluted cell density. In case of the control, every *E. coli* forms colonies, while in case of the wild type *Escherichia coli*, its growth is hampered. Comparatively, in case of the *E. coli* having the transcription factors comprising CRP Del 180 as the effector domains, it was confirmed to have grown well at a low temperature.

Among them, it is checked that the *E. coli* having the transcription factors of the CT1 and CT2 grew most satisfactorily at a low temperature, and the growth curve of CT1 at 15° C. is as shown in FIG. 14. The following is transcription factors of CT1 and CT2 indicating resistance to the low temperature (cold shock).

CT1=CRP 1~180a.a+Z19+Z6+Z22

CT2=CRP 1~180a.a+Z15+Z4+Z2

3-4. Induction of *E. coli* Having Resistance to Osmotic Pressure (High Salt Concentration)

The increase in osmotic pressure together with generation of overheat at fermentation degrade the productivity in expression of target proteins of a microorganism. Thus, *E. coli* having the resistance to osmotic pressure may be grown well, which have a high value as an industrial microorganism.

In this experimentation, in order to select *E. coli* having resistance to osmotic pressure, a minimum A medium in which 0.6M NaCl of high salt concentration ($K_2HPO_4$ 10.5 g/l, $KH_2PO_4$ 4.5 g/l, $(NH4)_2SO_4$ 1 g/l, sodium citrate $2H_2O$ 0.5 g/l, 20% glucose 10 ml/l, 1M $MgSO_47H_2O$ ml/l) was added was used. CRP Del 180 was used as the effector domain. After introducing the transcription factor library obtained in Experimental Example 2 to the *Escherichia coli*, XL1-Blue (Sambrook and Rusell, 2001), it was plated and cultivated at 37° C. Thereafter, *E. coli* having resistance to osmotic pressure was selected from the grown colonies. Transcription factors were isolated from the selected *Escherichia coli*, checked through the DNA sequence analysis, and re-transformed into *E. coli* in order to check whether resistance to the osmotic pressure was induced, thereby confirming activity of the transcription factors.

FIG. 15 shows the results of the experimentation. The left photo in FIG. 15 is a photo of a control of the *E. coli* grown in a minimum A medium to which osmotic pressure was not given, while the right photo shows a survivality of the *E. coli* in a minimum A medium to which osmotic pressure was given. 'C' in the photos indicates control *E. coli* having control plasmid in which artificial transcription factors were not encoded, while OT1, OT2, OT3 and OT4 indicate *E. coli* in which different artificial transcription factors were introduced, having resistance to osmotic pressure. The triangles at upper portions in FIG. 15 indicate a ×5 diluted cell density.

As shown in FIG. 15, under the optimum growth condition, every *E. coli* formed colonies, while under the osmotic pressure condition, growth of the wild-type *E. coli* was hampered but the *E. coli* having the transcription factors comprising the CRP Del 180 as the effector domains was grown well even under the osmotic pressure condition. Artificial transcription factors of OT1, OT2, OT3 and OT4 having resistance to osmotic pressure are as follows:

$OT1 = CRP\ 1\sim180a.a + Z24 + Z2 + Z2$ $OT2 = CRP\ 1\sim180a.a + Z8 + Z4 + Z19$ $OT3 = CRP\ 1\sim180a.a + Z5 + Z4 + Z17$ $OT4 = CRP\ 1\sim180a.a + Z9 + Z24 + Z23$

INDUSTRIAL APPLICABLE

As so far described, if various phenotypic changes are induced in the prokaryote by introducing the artificial transcription factors according to the present invention, it can be regulated to activate or repress gene expression of various prokaryotes by the introduced artificial transcription. From this, it can be induced various *E. coli* having the desired phenotypes by users, which is useful to provide customized *E. coli* for industries. In addition, it can be induced *E. coli* so that it can facilitate to analyze a unknown function of genes. Furthermore, *E. coli* having the desired characteristics can be induced, such as *E. coli* having the resistance to heat or cold shock, or osmotic pressure, or improvement of growth rate.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalents of such metes and bounds are therefore intended to be embraced by the appended claims.

What is claimed is:

1. An artificial transcription factor polypeptide which artificially activates or represses gene expression in prokaryotes, wherein the artificial transcription factor comprises one to three zinc finger domains fused to an effector domain comprising at least one truncated form of a catabolite regulatory protein (CRP);

wherein said truncated form of CRP is encoded by SEQ ID NO. 3 or encoded by SEQ ID NO. 5;

wherein the zinc finger domain(s) is (are) selected from the group consisting of:

Z1: zinc finger domain encoded by nucleic acid sequence of SEQ ID NO. 13;
Z2: zinc finger domain encoded by nucleic acid sequence of SEQ ID NO. 15;
Z3: zinc finger domain encoded by nucleic acid sequence of SEQ ID NO. 17;
Z4: zinc finger domain encoded by nucleic acid sequence of SEQ ID NO. 19;
Z5: zinc finger domain encoded by nucleic acid sequence of SEQ ID NO. 21;
Z6: zinc finger domain encoded by nucleic acid sequence of SEQ ID NO. 23;
Z7: zinc finger domain encoded by nucleic acid sequence of SEQ ID NO. 25;
Z8: zinc finger domain encoded by nucleic acid sequence of SEQ ID NO. 27;
Z9: zinc finger domain encoded by nucleic acid sequence of SEQ ID NO. 29;
Z10: zinc finger domain encoded by nucleic acid sequence of SEQ ID NO. 31;
Z11: zinc finger domain encoded by nucleic acid sequence of SEQ ID NO. 33;
Z12: zinc finger domain encoded by nucleic acid sequence of SEQ ID NO. 35;
Z13: zinc finger domain encoded by nucleic acid sequence of SEQ ID NO. 37;
Z14: zinc finger domain encoded by nucleic acid sequence of SEQ ID NO. 39;
Z15: zinc finger domain encoded by nucleic acid sequence of SEQ ID NO. 41;
Z16: zinc finger domain encoded by nucleic acid sequence of SEQ ID NO. 43;
Z17: zinc finger domain encoded by nucleic acid sequence of SEQ ID NO. 45;
Z18: zinc finger domain encoded by nucleic acid sequence of SEQ ID NO. 47;

Z19: zinc finger domain encoded by nucleic acid sequence of SEQ ID NO. 49;
Z20: zinc finger domain encoded by nucleic acid sequence of SEQ ID NO. 51;
Z21: zinc finger domain encoded by nucleic acid sequence of SEQ ID NO. 53;
Z22: zinc finger domain encoded by nucleic acid sequence of SEQ ID NO. 55;
Z23: zinc finger domain encoded by nucleic acid sequence of SEQ ID NO. 57;
Z24: zinc finger domain encoded by nucleic acid sequence of SEQ ID NO. 59;
Z25: zinc finger domain encoded by nucleic acid sequence of SEQ ID NO. 61; and
Z26: zinc finger domain encoded by nucleic acid sequence of SEQ ID NO. 63.

2. The artificial transcription factor polypeptide of claim 1,
wherein the zinc finger domains consist of Z13 encoded by SEQ ID NO. 37, Z2 encoded by SEQ ID NO.15 and Z23 encoded by SEQ ID NO. 57, and the truncated CRP is encoded by SEQ ID NO. 5; or
wherein the zinc finger domains consist of Z23 encoded by SEQ ID NO. 57, Z11 encoded by SEQ ID NO. 33 and Z19 encoded by SEQ ID NO. 49, and the truncated CRP is encoded by SEQ ID NO. 5; or
wherein the zinc finger domains consist of Z9 encoded by SEQ ID NO. 29, Z4 encoded by SEQ ID NO. 19 and Z11 encoded by SEQ ID NO. 33, and the truncated CRP is encoded by SEQ ID NO. 5; and
wherein said polypeptide, when contained in *E. coli*, increases resistance to heat shock.

3. The artificial transcription factor polypeptide of claim 1,
wherein the zinc finger domains consist of Z26 and encoded by SEQ ID NO. 63, and Z7 encoded by SEQ ID NO. 25, and the truncated CRP is encoded by SEQ ID NO. 5,
wherein said polypeptide, when contained in *E. coli*, results in improvement of growth.

4. The artificial transcription factor polypeptide of claim 1,
wherein said zinc finger domains consist of Z19 encoded by SEQ ID NO. 49, Z6 encoded by SEQ ID NO. No. 23 and Z22 encoded by SEQ ID NO. 55, and the truncated CRP is encoded by SEQ ID NO. 5; or
wherein said zinc finger domains consist of Z15 encoded by SEQ ID NO.41, Z4 encoded by SEQ ID NO. 9 and Z2 encoded by SEQ ID NO. 15, and the truncated CRP is encoded by SEQ ID NO. 5,
wherein said polypeptide, when contained in *E. coli*, confers increased resistance to cold.

5. The artificial transcription factor polypeptide of claim 1,
wherein said zinc finger domains consist of Z24 encoded by SEQ ID NO. 59, Z2 encoded by SEQ ID NO. 15 and Z2 encoded by SEQ ID NO. 15, and the truncated CRP is encoded by SEQ ID NO. 5; or
wherein the zinc finger domains consist of Z8 encoded by SEQ ID NO. 27, Z4 encoded by SEQ ID NO. 19 and Z19 encoded by SEQ ID NO. 49, and the truncated CRP is encoded by SEQ ID NO. 5; or
wherein the zinc finger domains consist of Z5 encoded by SEQ ID NO. 21, Z23 encoded by SEQ ID NO. 7 and Z17 encoded by SEQ ID NO. 45, and the truncated CRP is encoded by SEQ ID NO. 5; or
wherein the zinc finger domains consist of Z9 encoded by SEQ ID NO. 29, Z24 encoded by SEQ ID NO. 59 and Z23 encoded by SEQ ID NO. 57, and the truncated CRP is encoded by SEQ ID NO. 5,
wherein said polypeptide, when contained in *E. coli*, confers increased resistance to osmotic pressure.

* * * * *

SEQUENCE LISTING

```
<160> NUMBER OF SEQ ID NOS: 66

<210> SEQ ID NO 1
<211> LENGTH: 630
<212> TYPE: DNA
<213> ORGANISM: Escherichia coli
<220> FEATURE:
<221> NAME/KEY: misc_feature
<223> OTHER INFORMATION: CRP wild type
<220> FEATURE:
<221> NAME/KEY: CDS
<222> LOCATION: (1)...(630)

<400> SEQUENCE: 1 atg gtg ctt ggc aaa ccg caa aca gac ccg act ctc gaa tgg ttc ttg      48
Met Val Leu Gly Lys Pro Gln Thr Asp Pro Thr Leu Glu Trp Phe Leu
 1               5                  10                  15 tct cat tgc cac att cat aag tac cca tcc aag agc acg ctt att cac      96
Ser His Cys His Ile His Lys Tyr Pro Ser Lys Ser Thr Leu Ile His
             20                  25                  30 cag ggt gaa aaa gcg gaa acg ctg tac tac atc gtt aaa ggc tct gtg     144
Gln Gly Glu Lys Ala Glu Thr Leu Tyr Tyr Ile Val Lys Gly Ser Val
         35                  40                  45 gca gtg ctg atc aaa gac gaa gag ggt aaa gaa atg atc ctc tcc tat     192
Ala Val Leu Ile Lys Asp Glu Glu Gly Lys Glu Met Ile Leu Ser Tyr
     50                  55                  60 ctg aat cag ggt gat ttt att ggc gaa ctg ggc ctg ttt gaa gag ggc     240
Leu Asn Gln Gly Asp Phe Ile Gly Glu Leu Gly Leu Phe Glu Glu Gly
 65                  70                  75                  80 cag gaa cgt agc gca tgg gta cgt gcg aaa acc gcc tgt gaa gtg gct     288
Gln Glu Arg Ser Ala Trp Val Arg Ala Lys Thr Ala Cys Glu Val Ala
                 85                  90                  95 gaa att tcg tac aaa aaa ttt cgc caa ttg att cag gta aac ccg gac     336
Glu Ile Ser Tyr Lys Lys Phe Arg Gln Leu Ile Gln Val Asn Pro Asp
            100                 105                 110
```

```
att ctg atg cgt ttg tct gca cag atg gcg cgt cgt ctg caa gtc act        384
Ile Leu Met Arg Leu Ser Ala Gln Met Ala Arg Arg Leu Gln Val Thr
        115                 120                 125 tca gag aaa gtg ggc aac ctg gcg ttc ctc gac gtg acg ggc cgc att        432
Ser Glu Lys Val Gly Asn Leu Ala Phe Leu Asp Val Thr Gly Arg Ile
130                 135                 140 gca cag act ctg ctg aat ctg gca aaa caa cca gac gct atg act cac        480
Ala Gln Thr Leu Leu Asn Leu Ala Lys Gln Pro Asp Ala Met Thr His
145                 150                 155                 160 ccg gac ggt atg caa atc aaa att acc cgt cag gaa att ggt cag att        528
Pro Asp Gly Met Gln Ile Lys Ile Thr Arg Gln Glu Ile Gly Gln Ile
                165                 170                 175 gtc ggc tgt tct cgt gaa acc gtg gga cgc att ctg aag atg ctg gaa        576
Val Gly Cys Ser Arg Glu Thr Val Gly Arg Ile Leu Lys Met Leu Glu
            180                 185                 190 gat cag aac ctg atc tcc gca cac ggt aaa acc atc gtc gtt tac ggc        624
Asp Gln Asn Leu Ile Ser Ala His Gly Lys Thr Ile Val Val Tyr Gly
        195                 200                 205 act cgt                                                                630
Thr Arg
    210

<210> SEQ ID NO 2
<211> LENGTH: 210
<212> TYPE: PRT
<213> ORGANISM: Escherichia coli
<220> FEATURE:
<221> NAME/KEY: misc_feature
<223> OTHER INFORMATION: CRP wild type

<400> SEQUENCE: 2

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
        35                  40                  45

Ala Val Leu Ile Lys Asp Glu Glu Gly Lys Glu Met Ile Leu Ser Tyr
    50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
        115                 120                 125

Ser Glu Lys Val Gly Asn Leu Ala Phe Leu Asp Val Thr Gly Arg Ile
    130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
        195                 200                 205

Thr Arg
210
```

-continued

<210> SEQ ID NO 3
<211> LENGTH: 165
<212> TYPE: DNA
<213> ORGANISM: Escherichia coli
<220> FEATURE:
<221> NAME/KEY: misc_feature
<223> OTHER INFORMATION: CRP 137
<220> FEATURE:
<221> NAME/KEY: CDS
<222> LOCATION: (1)...(165)

<400> SEQUENCE: 3

```
atg ttc ctc gac gtg acg ggc cgc att gca cag act ctg ctg aat ctg      48
Met Phe Leu Asp Val Thr Gly Arg Ile Ala Gln Thr Leu Leu Asn Leu
  1               5                  10                  15 gca aaa caa cca gac gct atg act cac ccg gac ggt atg caa atc aaa      96
Ala Lys Gln Pro Asp Ala Met Thr His Pro Asp Gly Met Gln Ile Lys
                 20                  25                  30 att acc cgt cag gaa att ggt cag att gtc ggc tgt tct cgt gaa acc     144
Ile Thr Arg Gln Glu Ile Gly Gln Ile Val Gly Cys Ser Arg Glu Thr
             35                  40                  45 gtg gga cgc att ctg aag atg                                         165
Val Gly Arg Ile Leu Lys Met
 50                  55
```

<210> SEQ ID NO 4
<211> LENGTH: 55
<212> TYPE: PRT
<213> ORGANISM: Escherichia coli
<220> FEATURE:
<221> NAME/KEY: misc_feature
<223> OTHER INFORMATION: CRP 137

<400> SEQUENCE: 4

Met Phe Leu Asp Val Thr Gly Arg Ile Ala Gln Thr Leu Leu Asn Leu
  1               5                  10                  15

Ala Lys Gln Pro Asp Ala Met Thr His Pro Asp Gly Met Gln Ile Lys
                 20                  25                  30

Ile Thr Arg Gln Glu Ile Gly Gln Ile Val Gly Cys Ser Arg Glu Thr
             35                  40                  45

Val Gly Arg Ile Leu Lys Met
 50                  55

<210> SEQ ID NO 5
<211> LENGTH: 540
<212> TYPE: DNA
<213> ORGANISM: Escherichia coli
<220> FEATURE:
<221> NAME/KEY: misc_feature
<223> OTHER INFORMATION: CRP 180
<220> FEATURE:
<221> NAME/KEY: CDS
<222> LOCATION: (1)...(540)

<400> SEQUENCE: 5

```
atg gtg ctt ggc aaa ccg caa aca gac ccg act ctc gaa tgg ttc ttg      48
Met Val Leu Gly Lys Pro Gln Thr Asp Pro Thr Leu Glu Trp Phe Leu
  1               5                  10                  15 tct cat tgc cac att cat aag tac cca tcc aag agc acg ctt att cac      96
Ser His Cys His Ile His Lys Tyr Pro Ser Lys Ser Thr Leu Ile His
                 20                  25                  30 cag ggt gaa aaa gcg gaa acg ctg tac tac atc gtt aaa ggc tct gtg     144
Gln Gly Glu Lys Ala Glu Thr Leu Tyr Tyr Ile Val Lys Gly Ser Val
             35                  40                  45
```

```
gca gtg ctg atc aaa gac gaa gag ggt aaa gaa atg atc ctc tcc tat      192
Ala Val Leu Ile Lys Asp Glu Glu Gly Lys Glu Met Ile Leu Ser Tyr
 50                  55                  60 ctg aat cag ggt gat ttt att ggc gaa ctg ggc ctg ttt gaa gag ggc      240
Leu Asn Gln Gly Asp Phe Ile Gly Glu Leu Gly Leu Phe Glu Glu Gly
 65                  70                  75                  80 cag gaa cgt agc gca tgg gta cgt gcg aaa acc gcc tgt gaa gtg gct      288
Gln Glu Arg Ser Ala Trp Val Arg Ala Lys Thr Ala Cys Glu Val Ala
                 85                  90                  95 gaa att tcg tac aaa aaa ttt cgc caa ttg att cag gta aac ccg gac      336
Glu Ile Ser Tyr Lys Lys Phe Arg Gln Leu Ile Gln Val Asn Pro Asp
            100                 105                 110 att ctg atg cgt ttg tct gca cag atg gcg cgt cgt ctg caa gtc act      384
Ile Leu Met Arg Leu Ser Ala Gln Met Ala Arg Arg Leu Gln Val Thr
        115                 120                 125 tca gag aaa gtg ggc aac ctg gcg ttc ctc gac gtg acg ggc cgc att      432
Ser Glu Lys Val Gly Asn Leu Ala Phe Leu Asp Val Thr Gly Arg Ile
130                 135                 140 gca cag act ctg ctg aat ctg gca aaa caa cca gac gct atg act cac      480
Ala Gln Thr Leu Leu Asn Leu Ala Lys Gln Pro Asp Ala Met Thr His
145                 150                 155                 160 ccg gac ggt atg caa atc aaa att acc cgt cag gaa att ggt cag att      528
Pro Asp Gly Met Gln Ile Lys Ile Thr Arg Gln Glu Ile Gly Gln Ile
                165                 170                 175 gtc ggc tgt tct                                                      540
Val Gly Cys Ser
180
```

<210> SEQ ID NO 6
<211> LENGTH: 180
<212> TYPE: PRT
<213> ORGANISM: Escherichia coli
<220> FEATURE:
<221> NAME/KEY: misc_feature
<223> OTHER INFORMATION: CRP 180

<400> SEQUENCE: 6

```
Met Val Leu Gly Lys Pro Gln Thr Asp Pro Thr Leu Glu Trp Phe Leu
 1               5                  10                  15

Ser His Cys His Ile His Lys Tyr Pro Ser Lys Ser Thr Leu Ile His
                20                  25                  30

Gln Gly Glu Lys Ala Glu Thr Leu Tyr Tyr Ile Val Lys Gly Ser Val
         35                  40                  45

Ala Val Leu Ile Lys Asp Glu Glu Gly Lys Glu Met Ile Leu Ser Tyr
 50                  55                  60

Leu Asn Gln Gly Asp Phe Ile Gly Glu Leu Gly Leu Phe Glu Glu Gly
 65                  70                  75                  80

Gln Glu Arg Ser Ala Trp Val Arg Ala Lys Thr Ala Cys Glu Val Ala
                 85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
        115                 120                 125

Ser Glu Lys Val Gly Asn Leu Ala Phe Leu Asp Val Thr Gly Arg Ile
130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175
```

```
Val Gly Cys Ser
            180

<210> SEQ ID NO 7
<211> LENGTH: 137
<212> TYPE: DNA
<213> ORGANISM: Artificial Sequence
<220> FEATURE:
<223> OTHER INFORMATION: Chemically synthesized reporter plasmid
      pEGFP-A
<220> FEATURE:
<221> NAME/KEY: promoter
<222> LOCATION: (49)...(76)
<220> FEATURE:
<221> NAME/KEY: promoter
<222> LOCATION: (84)...(103)

<400> SEQUENCE: 7
atcgataagc ttgcggcggg ggcggcgggg actccccatc ccctgttga caattaatca      60 tcggctcgta taatgtgtgg aattgtgagc ggataacaat ttcacacagg aaacaggatc    120
aaattatgcc tgtcgac                                                    137

<210> SEQ ID NO 8
<211> LENGTH: 137
<212> TYPE: DNA
<213> ORGANISM: Artificial Sequence
<220> FEATURE:
<223> OTHER INFORMATION: Chemically synthesized reporter plasmid
      pEGFP-R
<220> FEATURE:
<221> NAME/KEY: promoter
<222> LOCATION: (29)...(56)
<220> FEATURE:
<221> NAME/KEY: promoter
<222> LOCATION: (64)...(83)

<400> SEQUENCE: 8
atcgataagc ttactcccca tccccctgtt gacaattaat catcggctcg tataatgtgt     60
ggaattgtga gcggataaca atttcgcggc gggggcggcg gggacacagg aaacaggatc    120
aaattatgcc tgtcgac                                                    137

<210> SEQ ID NO 9
<211> LENGTH: 72
<212> TYPE: DNA
<213> ORGANISM: Homo sapiens
<220> FEATURE:
<221> NAME/KEY: misc_feature
<223> OTHER INFORMATION: ZFP1 zinc finger of test transcription factors
<220> FEATURE:
<221> NAME/KEY: CDS
<222> LOCATION: (1)...(72)

<400> SEQUENCE: 9 gta tgc gat gta gag gga tgt acg tgg aaa ttt gcc cgc tca gat gag       48
Val Cys Asp Val Glu Gly Cys Thr Trp Lys Phe Ala Arg Ser Asp Glu
  1               5                  10                  15 ctc aac aga cac aag aaa agg cac                                       72
Leu Asn Arg His Lys Lys Arg His
             20

<210> SEQ ID NO 10
<211> LENGTH: 24
<212> TYPE: PRT
<213> ORGANISM: Homo sapiens
<220> FEATURE:
<221> NAME/KEY: misc_feature
<223> OTHER INFORMATION: ZFP1 zinc finger of test transcription factors
```

<400> SEQUENCE: 10

Val Cys Asp Val Glu Gly Cys Thr Trp Lys Phe Ala Arg Ser Asp Glu
 1               5                  10                  15

Leu Asn Arg His Lys Lys Arg His
            20

<210> SEQ ID NO 11
<211> LENGTH: 69
<212> TYPE: DNA
<213> ORGANISM: Homo sapiens
<220> FEATURE:
<221> NAME/KEY: misc_feature
<223> OTHER INFORMATION: ZFP2 zinc filter of experimental transcription
      factors
<220> FEATURE:
<221> NAME/KEY: CDS
<222> LOCATION: (1)...(69)

<400> SEQUENCE: 11 tat aag tgc atg gag tgt ggg aag gct ttt aac cgc agg tca cac ctc      48
Tyr Lys Cys Met Glu Cys Gly Lys Ala Phe Asn Arg Arg Ser His Leu
 1               5                  10                  15 aca cgg cac cag cgg att cac                                          69
Thr Arg His Gln Arg Ile His
            20

<210> SEQ ID NO 12
<211> LENGTH: 23
<212> TYPE: PRT
<213> ORGANISM: Homo sapiens
<220> FEATURE:
<221> NAME/KEY: misc_feature
<223> OTHER INFORMATION: ZFP2 zinc filter of experimental transcription
      factors

<400> SEQUENCE: 12

Tyr Lys Cys Met Glu Cys Gly Lys Ala Phe Asn Arg Arg Ser His Leu
 1               5                  10                  15

Thr Arg His Gln Arg Ile His
            20

<210> SEQ ID NO 13
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z1
<220> FEATURE:
<221> NAME/KEY: CDS
<222> LOCATION: (1)...(69)

<400> SEQUENCE: 13 cac atc tgc cat gaa tgt gga aag agt ttt gct caa agc tca ggc ctg      48
His Ile Cys His Glu Cys Gly Lys Ser Phe Ala Gln Ser Ser Gly Leu
 1               5                  10                  15 agt aaa cac agg aga atc cac                                          69
Ser Lys His Arg Arg Ile His
            20

<210> SEQ ID NO 14
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z1

<400> SEQUENCE: 14

His Ile Cys His Glu Cys Gly Lys Ser Phe Ala Gln Ser Ser Gly Leu
1               5                   10                  15

Ser Lys His Arg Arg Ile His
            20

<210> SEQ ID NO 15
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z2
<220> FEATURE:
<221> NAME/KEY: CDS
<222> LOCATION: (1)...(69)

<400> SEQUENCE: 15 tac gaa tgt gaa gag tgt ggc aaa gcc ttc att ggg agc tct gcc ctt    48
Tyr Glu Cys Glu Glu Cys Gly Lys Ala Phe Ile Gly Ser Ser Ala Leu
1               5                   10                  15 gtc att cat cag aga gtc cac                                        69
Val Ile His Gln Arg Val His
            20

<210> SEQ ID NO 16
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z2

<400> SEQUENCE: 16

Tyr Glu Cys Glu Glu Cys Gly Lys Ala Phe Ile Gly Ser Ser Ala Leu
1               5                   10                  15

Val Ile His Gln Arg Val His
            20

<210> SEQ ID NO 17
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z3
<220> FEATURE:
<221> NAME/KEY: CDS
<222> LOCATION: (1)...(69)

<400> SEQUENCE: 17 tat gag tgt gaa gaa tgt ggt aag gcc ttc agt cat agc tca gac ctt    48
Tyr Glu Cys Glu Glu Cys Gly Lys Ala Phe Ser His Ser Ser Asp Leu
1               5                   10                  15 atc aag cat cag aga acc cac                                        69
Ile Lys His Gln Arg Thr His
            20

<210> SEQ ID NO 18
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z3

<400> SEQUENCE: 18

-continued

```
Tyr Glu Cys Glu Glu Cys Gly Lys Ala Phe Ser His Ser Ser Asp Leu
1               5                   10                  15

Ile Lys His Gln Arg Thr His
            20
```

<210> SEQ ID NO 19
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z4
<220> FEATURE:
<221> NAME/KEY: CDS
<222> LOCATION: (1)...(69)

<400> SEQUENCE: 19

```
tat gag tgt gat gac tgt ggg aag acc ttc agc cag agc tgc agc ctc    48
Tyr Glu Cys Asp Asp Cys Gly Lys Thr Phe Ser Gln Ser Cys Ser Leu
1               5                   10                  15 ctt gaa cat cac aga atc cac                                        69
Leu Glu His His Arg Ile His
            20
```

<210> SEQ ID NO 20
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z4

<400> SEQUENCE: 20

```
Tyr Glu Cys Asp Asp Cys Gly Lys Thr Phe Ser Gln Ser Cys Ser Leu
1               5                   10                  15

Leu Glu His His Arg Ile His
            20
```

<210> SEQ ID NO 21
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z5
<220> FEATURE:
<221> NAME/KEY: CDS
<222> LOCATION: (1)...(69)

<400> SEQUENCE: 21

```
tat aaa tgt aat gag tgt gaa aga agt ttc act cag aat aca ggc ctc    48
Tyr Lys Cys Asn Glu Cys Glu Arg Ser Phe Thr Gln Asn Thr Gly Leu
1               5                   10                  15 att gaa cat caa aaa atc cac                                        69
Ile Glu His Gln Lys Ile His
            20
```

<210> SEQ ID NO 22
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z5

<400> SEQUENCE: 22

```
Tyr Lys Cys Asn Glu Cys Glu Arg Ser Phe Thr Gln Asn Thr Gly Leu
```

Ile Glu His Gln Lys Ile His
            20

<210> SEQ ID NO 23
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z6
<220> FEATURE:
<221> NAME/KEY: CDS
<222> LOCATION: (1)...(69)

<400> SEQUENCE: 23

```
tat cag tgt aat gcg tgt gga aaa ggc ttc acc cga att tca tac ctt     48
Tyr Gln Cys Asn Ala Cys Gly Lys Gly Phe Thr Arg Ile Ser Tyr Leu
 1               5                  10                  15 gtt caa cat cag aga agc cat                                         69
Val Gln His Gln Arg Ser His
            20
```

<210> SEQ ID NO 24
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z6

<400> SEQUENCE: 24

Tyr Gln Cys Asn Ala Cys Gly Lys Gly Phe Thr Arg Ile Ser Tyr Leu
 1               5                  10                  15

Val Gln His Gln Arg Ser His
            20

<210> SEQ ID NO 25
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z7
<220> FEATURE:
<221> NAME/KEY: CDS
<222> LOCATION: (1)...(69)

<400> SEQUENCE: 25

```
tat gaa tgt aat gag tgt ggg aag gta ttc agt tat agc tcc agc ctt     48
Tyr Glu Cys Asn Glu Cys Gly Lys Val Phe Ser Tyr Ser Ser Ser Leu
 1               5                  10                  15 atg gta cat cag aga acc cat                                         69
Met Val His Gln Arg Thr His
            20
```

<210> SEQ ID NO 26
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z7

<400> SEQUENCE: 26

Tyr Glu Cys Asn Glu Cys Gly Lys Val Phe Ser Tyr Ser Ser Ser Leu
 1               5                  10                  15

Met Val His Gln Arg Thr His
            20

<210> SEQ ID NO 27
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z8
<220> FEATURE:
<221> NAME/KEY: CDS
<222> LOCATION: (1)...(69)

<400> SEQUENCE: 27 tat gag tgt aat gag tgt ggg aag acc ttc agg caa acc tcc cag ctc       48
Tyr Glu Cys Asn Glu Cys Gly Lys Thr Phe Arg Gln Thr Ser Gln Leu
 1               5                  10                  15 att gtt cat ctc aga acc cac                                           69
Ile Val His Leu Arg Thr His
            20

<210> SEQ ID NO 28
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z8

<400> SEQUENCE: 28

Tyr Glu Cys Asn Glu Cys Gly Lys Thr Phe Arg Gln Thr Ser Gln Leu
 1               5                  10                  15

Ile Val His Leu Arg Thr His
            20

<210> SEQ ID NO 29
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z9
<220> FEATURE:
<221> NAME/KEY: CDS
<222> LOCATION: (1)...(69)

<400> SEQUENCE: 29 tat gaa tgc agt gag tgt gga aag gcc tat agg cac agc tcc cat ctc       48
Tyr Glu Cys Ser Glu Cys Gly Lys Ala Tyr Arg His Ser Ser His Leu
 1               5                  10                  15 att caa cac cag aga ctc cat                                           69
Ile Gln His Gln Arg Leu His
            20

<210> SEQ ID NO 30
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z9

<400> SEQUENCE: 30

Tyr Glu Cys Ser Glu Cys Gly Lys Ala Tyr Arg His Ser Ser His Leu
 1               5                  10                  15

Ile Gln His Gln Arg Leu His
            20

<210> SEQ ID NO 31
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z10
<220> FEATURE:
<221> NAME/KEY: CDS
<222> LOCATION: (1)...(69)

<400> SEQUENCE: 31 tat gaa tgc aat gag tgt gga gag gca ttc att cga agc aaa agt ctt    48
Tyr Glu Cys Asn Glu Cys Gly Glu Ala Phe Ile Arg Ser Lys Ser Leu
 1               5                  10                  15 gct cga cat cag gtc ctg cac                                        69
Ala Arg His Gln Val Leu His
            20

<210> SEQ ID NO 32
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z10

<400> SEQUENCE: 32

Tyr Glu Cys Asn Glu Cys Gly Glu Ala Phe Ile Arg Ser Lys Ser Leu
 1               5                  10                  15

Ala Arg His Gln Val Leu His
            20

<210> SEQ ID NO 33
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z11
<220> FEATURE:
<221> NAME/KEY: CDS
<222> LOCATION: (1)...(69)

<400> SEQUENCE: 33 tac aaa tgc aat gag tgt ggg aga gca ttc tgt tcc aat aga aat ctc    48
Tyr Lys Cys Asn Glu Cys Gly Arg Ala Phe Cys Ser Asn Arg Asn Leu
 1               5                  10                  15 att gac cat cag aga atc cac                                        69
Ile Asp His Gln Arg Ile His
            20

<210> SEQ ID NO 34
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z11

<400> SEQUENCE: 34

Tyr Lys Cys Asn Glu Cys Gly Arg Ala Phe Cys Ser Asn Arg Asn Leu
 1               5                  10                  15

Ile Asp His Gln Arg Ile His
            20

```
<210> SEQ ID NO 35
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z12
<220> FEATURE:
<221> NAME/KEY: CDS
<222> LOCATION: (1)...(69)

<400> SEQUENCE: 35 tat gag tgt agt gaa tgt ggc aaa gcc ttc agt cgg agt aaa tgt ctt      48
Tyr Glu Cys Ser Glu Cys Gly Lys Ala Phe Ser Arg Ser Lys Cys Leu
 1               5                  10                  15 att cga cat cag agc ctc cat                                           69
Ile Arg His Gln Ser Leu His
            20

<210> SEQ ID NO 36
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z12

<400> SEQUENCE: 36

Tyr Glu Cys Ser Glu Cys Gly Lys Ala Phe Ser Arg Ser Lys Cys Leu
 1               5                  10                  15

Ile Arg His Gln Ser Leu His
            20

<210> SEQ ID NO 37
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z13
<220> FEATURE:
<221> NAME/KEY: CDS
<222> LOCATION: (1)...(69)

<400> SEQUENCE: 37 ttt gaa tgt agc gag tgt ggt aag gca ttt ggt ctg agt aaa tgt ctt      48
Phe Glu Cys Ser Glu Cys Gly Lys Ala Phe Gly Leu Ser Lys Cys Leu
 1               5                  10                  15 att cgg cac cag aga ctt cac                                           69
Ile Arg His Gln Arg Leu His
            20

<210> SEQ ID NO 38
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z13

<400> SEQUENCE: 38

Phe Glu Cys Ser Glu Cys Gly Lys Ala Phe Gly Leu Ser Lys Cys Leu
 1               5                  10                  15

Ile Arg His Gln Arg Leu His
            20

<210> SEQ ID NO 39
<211> LENGTH: 66
```

-continued

```
<212> TYPE: DNA
<213> ORGANISM: Homo sapiens
<220> FEATURE:
<221> NAME/KEY: misc_feature
<223> OTHER INFORMATION: zinc finger domain Z14
<220> FEATURE:
<221> NAME/KEY: CDS
<222> LOCATION: (1)...(66)

<400> SEQUENCE: 39 aaa tgt aag caa tgt ggg aaa gct ttt gga tgt ccc tca aac ctt cga      48
Lys Cys Lys Gln Cys Gly Lys Ala Phe Gly Cys Pro Ser Asn Leu Arg
 1               5                  10                  15 agg cat gga agg act cac                                              66
Arg His Gly Arg Thr His
            20

<210> SEQ ID NO 40
<211> LENGTH: 22
<212> TYPE: PRT
<213> ORGANISM: Homo sapiens
<220> FEATURE:
<221> NAME/KEY: misc_feature
<223> OTHER INFORMATION: zinc finger domain Z14

<400> SEQUENCE: 40

Lys Cys Lys Gln Cys Gly Lys Ala Phe Gly Cys Pro Ser Asn Leu Arg
 1               5                  10                  15

Arg His Gly Arg Thr His
            20

<210> SEQ ID NO 41
<211> LENGTH: 66
<212> TYPE: DNA
<213> ORGANISM: Homo sapiens
<220> FEATURE:
<221> NAME/KEY: misc_feature
<223> OTHER INFORMATION: zinc finger domain Z15
<220> FEATURE:
<221> NAME/KEY: CDS
<222> LOCATION: (1)...(66)

<400> SEQUENCE: 41 aag tgt aag gag tgt ggg aaa gcc ttc aac cac agc tcc aac ttc aat      48
Lys Cys Lys Glu Cys Gly Lys Ala Phe Asn His Ser Ser Asn Phe Asn
 1               5                  10                  15 aaa cac cac aga atc cac                                              66
Lys His His Arg Ile His
            20

<210> SEQ ID NO 42
<211> LENGTH: 22
<212> TYPE: PRT
<213> ORGANISM: Homo sapiens
<220> FEATURE:
<221> NAME/KEY: misc_feature
<223> OTHER INFORMATION: zinc finger domain Z15

<400> SEQUENCE: 42

Lys Cys Lys Glu Cys Gly Lys Ala Phe Asn His Ser Ser Asn Phe Asn
 1               5                  10                  15

Lys His His Arg Ile His
            20

<210> SEQ ID NO 43
<211> LENGTH: 72
<212> TYPE: DNA
<213> ORGANISM: Homo sapiens
```

```
<220> FEATURE:
<221> NAME/KEY: misc_feature
<223> OTHER INFORMATION: zinc finger domain Z16
<220> FEATURE:
<221> NAME/KEY: CDS
<222> LOCATION: (1)...(72)

<400> SEQUENCE: 43 gta tgc gat gta gag gga tgt acg tgg aaa ttt gcc cgc tca gat gag    48
Val Cys Asp Val Glu Gly Cys Thr Trp Lys Phe Ala Arg Ser Asp Glu
 1               5                  10                  15 ctc aac aga cac aag aaa agg cac                                    72
Leu Asn Arg His Lys Lys Arg His
             20

<210> SEQ ID NO 44
<211> LENGTH: 24
<212> TYPE: PRT
<213> ORGANISM: Homo sapiens
<220> FEATURE:
<221> NAME/KEY: misc_feature
<223> OTHER INFORMATION: zinc finger domain Z16

<400> SEQUENCE: 44

Val Cys Asp Val Glu Gly Cys Thr Trp Lys Phe Ala Arg Ser Asp Glu
 1               5                  10                  15

Leu Asn Arg His Lys Lys Arg His
             20

<210> SEQ ID NO 45
<211> LENGTH: 66
<212> TYPE: DNA
<213> ORGANISM: Homo sapiens
<220> FEATURE:
<221> NAME/KEY: misc_feature
<223> OTHER INFORMATION: zinc finger domain Z17
<220> FEATURE:
<221> NAME/KEY: CDS
<222> LOCATION: (1)...(66)

<400> SEQUENCE: 45 gag tgt aat tac tgt gga aaa acc ttt agt gtg agc tca acc ctt att    48
Glu Cys Asn Tyr Cys Gly Lys Thr Phe Ser Val Ser Ser Thr Leu Ile
 1               5                  10                  15 aga cat cag aga atc cac                                            66
Arg His Gln Arg Ile His
             20

<210> SEQ ID NO 46
<211> LENGTH: 22
<212> TYPE: PRT
<213> ORGANISM: Homo sapiens
<220> FEATURE:
<221> NAME/KEY: misc_feature
<223> OTHER INFORMATION: zinc finger domain Z17

<400> SEQUENCE: 46

Glu Cys Asn Tyr Cys Gly Lys Thr Phe Ser Val Ser Ser Thr Leu Ile
 1               5                  10                  15

Arg His Gln Arg Ile His
             20

<210> SEQ ID NO 47
<211> LENGTH: 69
<212> TYPE: DNA
<213> ORGANISM: Homo sapiens
<220> FEATURE:
<221> NAME/KEY: misc_feature
```

<223> OTHER INFORMATION: zinc finger domain Z18
<220> FEATURE:
<221> NAME/KEY: CDS
<222> LOCATION: (1)...(69)

<400> SEQUENCE: 47

```
tat gca tgt cat cta tgt gga aaa gcc ttc act cag agt tct cac ctt      48
Tyr Ala Cys His Leu Cys Gly Lys Ala Phe Thr Gln Ser Ser His Leu
  1               5                  10                  15 aga aga cat gag aaa act cac                                          69
Arg Arg His Glu Lys Thr His
             20
```

<210> SEQ ID NO 48
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z18

<400> SEQUENCE: 48

```
Tyr Ala Cys His Leu Cys Gly Lys Ala Phe Thr Gln Ser Ser His Leu
  1               5                  10                  15

Arg Arg His Glu Lys Thr His
             20
```

<210> SEQ ID NO 49
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z19
<220> FEATURE:
<221> NAME/KEY: CDS
<222> LOCATION: (1)...(69)

<400> SEQUENCE: 49

```
tat gaa tgt aac aca tgc agg aaa acc ttc tct caa aag tca aat ctc      48
Tyr Glu Cys Asn Thr Cys Arg Lys Thr Phe Ser Gln Lys Ser Asn Leu
  1               5                  10                  15 att gta cat cag aga aca cac                                          69
Ile Val His Gln Arg Thr His
             20
```

<210> SEQ ID NO 50
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z19

<400> SEQUENCE: 50

```
Tyr Glu Cys Asn Thr Cys Arg Lys Thr Phe Ser Gln Lys Ser Asn Leu
  1               5                  10                  15

Ile Val His Gln Arg Thr His
             20
```

<210> SEQ ID NO 51
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z20
<220> FEATURE:

```
<221> NAME/KEY: CDS
<222> LOCATION: (1)...(69)

<400> SEQUENCE: 51 tat aag tgc cct gat tgt ggg aag agt ttt agt cag agt tcc agc ctc      48
Tyr Lys Cys Pro Asp Cys Gly Lys Ser Phe Ser Gln Ser Ser Ser Leu
 1               5                  10                  15 att cgc cac cag cgg aca cac                                          69
Ile Arg His Gln Arg Thr His
            20

<210> SEQ ID NO 52
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z20

<400> SEQUENCE: 52

Tyr Lys Cys Pro Asp Cys Gly Lys Ser Phe Ser Gln Ser Ser Ser Leu
 1               5                  10                  15

Ile Arg His Gln Arg Thr His
            20

<210> SEQ ID NO 53
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z21
<220> FEATURE:
<221> NAME/KEY: CDS
<222> LOCATION: (1)...(69)

<400> SEQUENCE: 53 tat aag tgc atg gag tgt ggg aag gct ttt aac cgc agg tca cac ctc      48
Tyr Lys Cys Met Glu Cys Gly Lys Ala Phe Asn Arg Arg Ser His Leu
 1               5                  10                  15 aca cgg cac cag cgg att cac                                          69
Thr Arg His Gln Arg Ile His
            20

<210> SEQ ID NO 54
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z21

<400> SEQUENCE: 54

Tyr Lys Cys Met Glu Cys Gly Lys Ala Phe Asn Arg Arg Ser His Leu
 1               5                  10                  15

Thr Arg His Gln Arg Ile His
            20

<210> SEQ ID NO 55
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z22
<220> FEATURE:
<221> NAME/KEY: CDS
<222> LOCATION: (1)...(69)
```

-continued

<400> SEQUENCE: 55

```
tat aca tgt aaa cag tgt ggg aaa gcc ttc agt gtt tcc agt tcc ctt        48
Tyr Thr Cys Lys Gln Cys Gly Lys Ala Phe Ser Val Ser Ser Ser Leu
 1               5                  10                  15 cga aga cat gaa acc act cac                                            69
Arg Arg His Glu Thr Thr His
            20
```

<210> SEQ ID NO 56
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z22

<400> SEQUENCE: 56

```
Tyr Thr Cys Lys Gln Cys Gly Lys Ala Phe Ser Val Ser Ser Ser Leu
 1               5                  10                  15

Arg Arg His Glu Thr Thr His
            20
```

<210> SEQ ID NO 57
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z23
<220> FEATURE:
<221> NAME/KEY: CDS
<222> LOCATION: (1)...(69)

<400> SEQUENCE: 57

```
tac aaa tgt gaa gaa tgt ggc aaa gcc ttt agg cag tcc tca cac ctt        48
Tyr Lys Cys Glu Glu Cys Gly Lys Ala Phe Arg Gln Ser Ser His Leu
 1               5                  10                  15 act aca cat aag ata att cat                                            69
Thr Thr His Lys Ile Ile His
            20
```

<210> SEQ ID NO 58
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z23

<400> SEQUENCE: 58

```
Tyr Lys Cys Glu Glu Cys Gly Lys Ala Phe Arg Gln Ser Ser His Leu
 1               5                  10                  15

Thr Thr His Lys Ile Ile His
            20
```

<210> SEQ ID NO 59
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z24
<220> FEATURE:
<221> NAME/KEY: CDS
<222> LOCATION: (1)...(69)

<400> SEQUENCE: 59

```
tat gag tgt cac gat tgc gga aag tcc ttt agg cag agc acc cac ctc        48
Tyr Glu Cys His Asp Cys Gly Lys Ser Phe Arg Gln Ser Thr His Leu
  1               5                  10                  15 act cgg cac cgg agg atc cac                                            69
Thr Arg His Arg Arg Ile His
            20
```

<210> SEQ ID NO 60
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z24

<400> SEQUENCE: 60

```
Tyr Glu Cys His Asp Cys Gly Lys Ser Phe Arg Gln Ser Thr His Leu
  1               5                  10                  15

Thr Arg His Arg Arg Ile His
            20
```

<210> SEQ ID NO 61
<211> LENGTH: 75
<212> TYPE: DNA
<213> ORGANISM: Homo sapiens
<220> FEATURE:
<221> NAME/KEY: misc_feature
<223> OTHER INFORMATION: zinc finger domain Z25
<220> FEATURE:
<221> NAME/KEY: CDS
<222> LOCATION: (1)...(75)

<400> SEQUENCE: 61

```
tac cac tgt gac tgg gac ggc tgt gga tgg aaa ttc gcc cgc tca gat        48
Tyr His Cys Asp Trp Asp Gly Cys Gly Trp Lys Phe Ala Arg Ser Asp
  1               5                  10                  15 gaa ctg acc agg cac tac cgt aaa cac                                    75
Glu Leu Thr Arg His Tyr Arg Lys His
            20                  25
```

<210> SEQ ID NO 62
<211> LENGTH: 25
<212> TYPE: PRT
<213> ORGANISM: Homo sapiens
<220> FEATURE:
<221> NAME/KEY: misc_feature
<223> OTHER INFORMATION: zinc finger domain Z25

<400> SEQUENCE: 62

```
Tyr His Cys Asp Trp Asp Gly Cys Gly Trp Lys Phe Ala Arg Ser Asp
  1               5                  10                  15

Glu Leu Thr Arg His Tyr Arg Lys His
            20                  25
```

<210> SEQ ID NO 63
<211> LENGTH: 69
<212> TYPE: DNA
<213> ORGANISM: Homo sapiens
<220> FEATURE:
<221> NAME/KEY: misc_feature
<223> OTHER INFORMATION: zinc finger domain Z26
<220> FEATURE:
<221> NAME/KEY: CDS
<222> LOCATION: (1)...(69)

<400> SEQUENCE: 63

```
ttc cag tgt aaa act tgt cag cga aag ttc tcc cgg tcc gac cac ctg        48
```

```
Phe Gln Cys Lys Thr Cys Gln Arg Lys Phe Ser Arg Ser Asp His Leu
 1               5                  10                  15 aag acc cac acc agg act cat                                              69
Lys Thr His Thr Arg Thr His
                20

<210> SEQ ID NO 64
<211> LENGTH: 23
<212> TYPE: PRT
<213> ORGANISM: Homo sapiens
<220> FEATURE:
<221> NAME/KEY: misc_feature
<223> OTHER INFORMATION: zinc finger domain Z26

<400> SEQUENCE: 64

Phe Gln Cys Lys Thr Cys Gln Arg Lys Phe Ser Arg Ser Asp His Leu
 1               5                  10                  15

Lys Thr His Thr Arg Thr His
                20

<210> SEQ ID NO 65
<211> LENGTH: 9
<212> TYPE: PRT
<213> ORGANISM: Artificial Sequence
<220> FEATURE:
<223> OTHER INFORMATION: chemically synthesized peptide linker

<400> SEQUENCE: 65

Thr Gly Glu Gln Lys Arg Pro Tyr Phe
 1               5

<210> SEQ ID NO 66
<211> LENGTH: 6
<212> TYPE: PRT
<213> ORGANISM: Artificial Sequence
<220> FEATURE:
<223> OTHER INFORMATION: chemically synthesized peptide linker

<400> SEQUENCE: 66

Thr Gly Glu Lys Pro Tyr
 1               5
```